(12) United States Patent
Munusamy et al.

(10) Patent No.: US 9,580,363 B2
(45) Date of Patent: Feb. 28, 2017

(54) NITROGEN-FIXING BACTERIAL INOCULANT FOR IMPROVEMENT OF CROP PRODUCTIVITY AND REDUCTION OF NITROUS OXIDE EMISSION

(71) Applicant: TEMASEK LIFE SCIENCES LABORATORY LIMITED, Singapore (SG)

(72) Inventors: Madhaiyan Munusamy, Singapore (SG); Lianghui Ji, Singapore (SG)

(73) Assignee: TEMASEK LIFE SCIENCES LABORATORY LIMITED, Singapore (SG)

( * ) Notice: Subject to any disclaimer, the term of this patent is extended or adjusted under 35 U.S.C. 154(b) by 0 days.

(21) Appl. No.: 14/386,673

(22) PCT Filed: Mar. 20, 2013

(86) PCT No.: PCT/SG2013/000112
§ 371 (c)(1),
(2) Date: Sep. 19, 2014

(87) PCT Pub. No.: WO2013/141815
PCT Pub. Date: Sep. 26, 2013

(65) Prior Publication Data
US 2015/0101373 A1  Apr. 16, 2015

Related U.S. Application Data

(60) Provisional application No. 61/613,579, filed on Mar. 21, 2012.

(51) Int. Cl.
| | | |
|---|---|---|
| C12N 1/20 | (2006.01) | |
| A01N 63/00 | (2006.01) | |
| C05F 11/08 | (2006.01) | |
| C12N 9/02 | (2006.01) | |
| C12R 1/01 | (2006.01) | |
| C05D 9/02 | (2006.01) | |

(52) U.S. Cl.
CPC ............ *C05F 11/08* (2013.01); *A01N 63/00* (2013.01); *C05D 9/02* (2013.01); *C12N 1/20* (2013.01); *C12N 9/0095* (2013.01); *C12N 9/0097* (2013.01); *C12R 1/01* (2013.01); *C12Y 118/06001* (2013.01); *C12Y 119/06001* (2013.01); *Y02P 60/218* (2015.11)

(58) Field of Classification Search
None
See application file for complete search history.

(56) References Cited

U.S. PATENT DOCUMENTS

| 7,214,509 B2 | 5/2007 | Schnoor et al. |
| 2011/0028321 A1 | 2/2011 | Tani et al. |

OTHER PUBLICATIONS

Shen Bing-Fu et al (Acta Phytophysiologica Sinica, (1995) vol. 21, No. 3, Abstract Only).*
Fuji et al (Plant and Soil (1987), vol. 103, No. 2, pp. 221-226.*
Mehnaz et al (Canadian Journal of Microbiology (2001), vol. 47, No. 2, pp. 110-117).*
Chincholkar et al. Abstract Only. Sep. 2006. Accession No. 2006-082054 [Sep. 2006] 2003MU01274 A Jun. 10, 2005 (Sep. 2006).*
Madhaiyan, M. et al., "Nodulation and Plant-Growth Promotion by Methylotrophic Bacteria Isolated from Tropical Legumes," Microbiological Research, vol. 164 (2009), pp. 114-120.
Cardoso, J.D. et al., "Polyphasic Approach for the Characterization of Rhizobial Symbionts Effective in Fixing N2 with Common Bean (*Phaseolus vulgaris* L.)," Applied Genetics and Molecular Biotechnology, vol. 93 (2012), pp. 2035-2049, © Springer-Verlag 2011.
Lee, H.S. et al., "Physiological Enhancement of Early Growth of Rice Seedlings (*Oryza sativa* L) by Production of Phytohormone of N2-Fixing Methylotrophic Isolates," Biology and Fertility of Soils, vol. 42, (2006), pp. 402-408, © Springer-Verlag 2006.
Adhikari, T.B. et al., "Evaluation of Bateria Isolated from Rice for Plant Growth Promotion and Biological Control of Seedling Disease of Rice," Canadian Journal of Microbiology, vol. 47, (2001), pp. 916-924, © 2001 NRC Canada.
Xie, C.H. et al., "*Pleomorphomonas oryzae* Gen. Nov., sp. nov., a Nitrogen-Fixing Bacterium Isolated from Paddy Soil of *Oryza sativa*," International Journal of Systematic and Evolutionary Microbiology, (2005), vol. 55, pp. 1233-1237, © 2005 IUMS.
Madhaiyan, M. et al., "Regulation of Ethylene Levels in Canola (*Brassica campestris*) by 1-Aminocyclopropane-1-Carboxylate Deaminase-Containing Methylobacterium Fujisawaense," Planta, (2006), vol. 224, pp. 268-278, © Springer-Verlag 2006.
Madhaiyan, M. et al., "*Pleomorphormonas diazotrophica* sp. nov., a Novel Endophytic N-Fixing Bacterium Isolated from the Root Tissue of *Jatropha curcas* L," International Journal of Systematic and Evolutionary Microbiology7 Dec. 2012, Abstract, 1 page.
Madhaiyan, M. et al., Genbank Accession No. JQ346801.1, "*Pleomorphomonas* sp. R5-392 16S Ribosomal RNA Gene, Partial Sequence," May 15, 2013, 1 page.
Madhaiyan, M. et al., Genbank Accession No. JQ660218, "*Sphingomonas yunnanensis* Strain S6-274 16S Ribosomal RNA Gene, Partial Sequence," Apr. 10, 2012, 1 page.
Madhaiyan, M. et al., Genbank Accession No. JQ659310, "*Methylobacterium* sp. L2-4 16S Ribosomal RNA Gene, Partial Sequence," Apr. 10, 2012, 1 page.

(Continued)

*Primary Examiner* — Jennifer Graser
(74) *Attorney, Agent, or Firm* — Rothwell, Figg, Ernst & Manbeck, P.C.

(57) ABSTRACT

The present invention relates to methods of reducing chemical fertilizer usage and greenhouse gas nitrous oxide emission and to methods of improving plant growth rate and seed productivity in agriculture through the application of a novel artificially manufactured formula containing a nitrogen-fixing bacterium that efficiently colonizes non-legume plants in aerial parts and the root system. The bacteria inocula and methods are particularly suitable for plants in the genera *Jatropha, Sorghum, Gossypium, Elaeis, Ricinus, Oryza* and *Manihot*.

26 Claims, 5 Drawing Sheets

(56) References Cited

OTHER PUBLICATIONS

Madhaiyan, M. et al., Genbank Accession No. JQ659313, "*Methylbacterium populi* Strain L2-76 16S Ribosomal RNA Gene, Partial Sequence," Apr. 10, 2012, 1 page.
Madhaiyan, M. et al., Genbank Accession No. JQ659688.1, "*Enterobacter* sp. R4-368 16S Ribosomal RNA Gene, Partial Sequence," Apr. 10, 2012, 2 pages.
International Search Report, PCT/SG013/000112, May 3, 2013, 8 pages.

* cited by examiner

X13303
24206 bp

R4-368 Contig 27 NifCluster
31707 bp

L2-4 contig 00028 nif-like genes
14752 bp

NITROGEN-FIXING BACTERIAL INOCULANT FOR IMPROVEMENT OF CROP PRODUCTIVITY AND REDUCTION OF NITROUS OXIDE EMISSION

CROSS-REFERENCE OF THE RELATED APPLICATION

The present application is a 35 U.S.C.§371 National Phase Entry Application of PCT/SG2013/000112, filed 20 Mar. 2013, and designating the United States, which in turn claims priority from U.S. Provisional Application No. 61/613,579 filed 21 Mar. 2012. Each application is incorporated herein by reference in its entirety.

SEQUENCE SUBMISSION

The present application is being filed along with a Sequence Listing in electronic format. The Sequence Listing is entitled 2577211PCTSequenceListing.txt, created on 25 Jan. 2013 and is 49 kb in size. The information in the electronic format of the Sequence Listing is incorporated herein by reference in its entirety.

BACKGROUND OF THE INVENTION

The present invention relates to methods of reducing chemical fertilizer usage and greenhouse gas nitrous oxide ($N_2O$) emission and to methods of improving plant growth rate and seed productivity in agriculture through the application of a novel artificially manufactured formula containing a nitrogen-fixing bacterium that efficiently colonizes non-legume plants in aerial parts and the root system. The bacteria inocula and methods are particularly suitable for plants in the genera *Jatropha, Sorghum, Gossypium, Elaeis, Oryza, Ricinus* and *Manihot*.

The rapid rise in fossil fuel price, the fast diminishment of global fuel and the concern about rapid global warming resulted from the accumulation of atmospheric greenhouse gas have served as the three catalysts in the recent biofuel boom (Chang, 2007). The environmental benefit of biofuel consumption is attributed from the widely believed outcome of reduced greenhouse gas ($CO_2$) emission.

Recently, a new issue that has been brought up for debate regarding the benefit of biofuels. Nitrous oxide is produced naturally in the soil during the microbial processes of nitrification and denitrification. A significant percentage of the nitrogen fertilizer used in biofuel production is converted to reactive nitrogen $N_2O$, a greenhouse gas which has 310 times the ability to trap heat in the atmosphere (Barton and Atwater, 2002). The benefit of $CO_2$ mitigation through biofuel consumption will be cancelled out if the use of N-fertilizer is not controlled (Galloway et al., 2008; Melillo et al, 2009; Crutzen et al., 2008).

Application of nitrogen fertilizer has become an essential practice in modern agriculture as it is vital to maintain competitive crop productivity. It has been well known that legumes require much less input of nitrogen fertilizer owing to the presence of nitrogen-fixing structure called nodules, in which nitrogen-fixing microorganisms (diazotrophs), mostly belonging to species in the *Rhizobium, Sinorhizobium, Mesorhizobium* and *Bradyrhizobium* genera (Jourand et al., 2004; Kaneko et al., 2000; Stacey et al., 1991; Gottfert et al., 2001), form a mutually beneficial symbiotic relationship with the bacteria supplying nitrogen source to the plants while drawing carbon source from the plants cells (Long, 1996; Young and Johnston, 1989). Some exception has been found recently. For example, *Methylobacterium nodulans* is the root nodule-inducing agent for some species in the genus *Crotalaria*, a leguminous plant (Renier et al., 2011; Jourand et al., 2005) and nitrogen-fixing nodules may develop in stem tissues of some legumes (Eaglesham and Szalay, 1983; Dreyfus and Dommergues, 1981). Frankia, Gram-positive soil bacteria also induce the formation of nitrogen-fixing root nodules in a few species in the Rosaceae family (Moir et al., 2011).

The formation of symbiotic nodules involves with complex genetic and chemical interactions between the diazotroph and host. For example, the symbiosis between *Sinorhizobium meliloti* and its plant hosts begins when the plant secretes an array of betaines and flavonoids into the rhizosphere: 4,4'-dihydroxy-2'-methoxychalcone, chrysoeriol, cynaroside, 4',7-dihydroxyflavone, 6"-O-malonylononin, liquiritigenin, luteolin, 3',5-dimethoxyluteolin, 5-methoxyluteolin, medicarpin, stachydrine, trigonelline. These compounds attract *S. meliloti* to the surface of the root hairs of the plant where the bacteria begin secreting nodulation factor (Peters et al., 1986; Maxwell et al., 1989). As a consequence, symbiotic nodule-forming nitrogen-fixation is found almost exclusively in legume species. Bradyrhizobia and rhizobia share characteristics with plant growth promoting rhizobacteria (PGPR). Nodule inducing bacteria, like other PGPR, are capable of colonizing the roots of non-legume plants (Antoun et al., 1998).

Diazotrophs have been found in free-living bacteria, among which *Azotobacter vinelandii* is the best studied. An increasingly number of diazotrophic species, e.g., *Azospirillum, Herbaspirillum, Burkholderia, Gluconacetobacter*, have been reported to form atypical symbiotic relationship with plants (Zehr, 2011; Radiers et al., 2004; Pedraza, 2008). They often grow on the surface root system (rhizobacteria) although some are able to infect plant tissues (endophytic bacteria) and perform nitrogen fixation, which is also able promote plant growth. For example, U.S. Pat. No. 7,393,678 B2 describes strains of *Klebsiella pneumonia*, which colonize the root surface (Liu et al., 2011), are able to promote growth of cereals (wheat and corn) either in the presence or absence of chemical nitrogen application. However, only specially isolated mutant strains of *Klebsiella pneumonia* were able to perform satisfactory plant growth promoting function as the nitrogen-fixation activity is low in majority of strains. Perhaps, the best examples of endophytic nitrogen-fixation can be found in sugarcane and wild rice, with *Herbaspirillum, Gluconacetobacter, Enterobacter, Azospirillum, Swaminathania* and *Acetobacter* being the possible contributors of nitrogen-fixing species (Pedraza, 2008; Boddey et al., 1995; Baldani et al., 2002; Elbeltagy et al., 2001; Saravanan et al., 2008). Photosynthetic Bradyrhizobia are the natural endophytes of the African wild rice *Oryza breviligulata* while the intercellular colonization and growth-promoting effects of a *Methylobacterium* sp. was observed in common rice *Oryza sativa* L. Cv CO-43 although the later was believed to resulted from phytohormone secretion of the bacterium (Senthilkumar et al., 2009; Chaintreuil et al., 2000).

A study of Azospirilla indicates that, similar to nodulation and nitrogen-fixation in legumes, the endophytic colonization process is genetically controlled and exopolysaccharide production inhibits both endophytic colonization and nitrogen fixation in common wheat seedlings (Kennedy et al., 1997). In addition, a mutation that blocks exopolysaccharide synthesis prevents nodulation of peas by *Rhizobium leguminosarum* but not of beans by *R. phaseoli* (Borthakur et al., 1986). Therefore, the ability of a diazotroph to promote plant growth via nitrogen-fixation is not predictable from its performance in other plants.

*Jatropha curcas* is a small woody plant belonging to the Euphorbiaceae family. Several unique characteristics make it an ideal plant for biodiesel production (Fairless, 2007; Gaydou et al., 1982; Openshaw, 2000). These include the ability to grow on marginal land; low requirement for water; a non-food crop status and fast oil production in 0.5-2 years after planting compared to more than 3 years for oil palm. Accordingly, several Asian countries, particularly Indonesian and India, have made ambitious plans to promote jatropha plantation. Several other plants have also attracted strong interest as alternative crop for biofuel production. These include castor bean, sorghum, and sweet sorghum.

As *Jatropha* is targeted to marginal land where soil nutrient is low, the requirement for nitrogen fertilizer will be higher than other crops. Therefore, any technology that reduces nitrogen fertilizer usage will be highly desirable. Today there is little research on naturally occurring diazotrophs in *Jatropha* nor the application of these microbes for improvement of plant productivity. Similar situations can be found in other crops, such as *Sorghum*, castor bean and cassava.

SUMMARY OF THE INVENTION

The present invention relates to methods of reducing chemical fertilizer usage and greenhouse gas nitrous oxide emission and to methods of improving plant growth rate and seed productivity in agriculture through the application of a novel artificially manufactured formula containing a nitrogen-fixing bacterium that efficiently colonizes non-legume plants in aerial parts and root system. The bacteria inocula and methods are particularly suitable for plants in the genera *Jatropha, Sorghum, Gossypium, Elaeis, Oryza, Ricinus* and *Manihot*.

In a first aspect, the present invention provides a biologically pure culture of a bacterial species selected from the *Enterobacter, Methylobacterium, Sphingomonas*, and *Pleomorphomonas* genera as described herein. In some embodiments, the bacterial species of the present invention are able to efficiently reduce atmospheric $N_2$ to ammonia as evidenced by the acetylene reduction assay (AR assay) in planta. In some embodiments, the $N_2$ reduction occurs on the leaf surface. In other embodiments, the $N_2$ reduction occurs inside the leaf surface. In additional embodiments, the $N_2$ reduction occurs on the surface of the roots or root system. In further embodiments, the $N_2$ reduction occurs inside the root tissue. In some embodiments, the bacterial species is able to self-propagate efficiently on the leaf surface, root surface or inside plant tissues without inducing a noticeable plant defense reaction, such as cell death. In other embodiments, bacterial species of the present invention can be isolated by culturing a plant tissue extract or leaf surface wash in a medium with no added nitrogen source as described herein.

In one embodiment, the genomic DNA of the bacterial species shares least 97% and preferably at least 98% identity to SEQ ID NO:10. In some embodiments, the bacterial species is an *Enterobacter* species containing a set of genes required for nitrogen-fixation. In some embodiments, the Enterobacter species produces substantial amounts of extracellular polysaccharide (EPS), or endoglucanase. In another embodiment, the genomic DNA of the bacterial species shares 97% and preferably at least 98% identity to SEQ ID NO:11. In some embodiments, the bacterial species is a *Pleomorphomonas* species in which the nitrogen-fixing capability is stimulated by about 0.1 mM to about 0.5 mM of $NH_4^+$ ion. In an additional embodiment, the genomic DNA of the bacterial species shares 97% and preferably at least 98% identity homology to SEQ ID NO:12. In some embodiments, the bacterial species is a *Sphingomonas* species that is able to grow in nitrogen-free medium. In a further embodiment, the genomic DNA of the bacterial species shares 97% and preferably at least 98% identity to SEQ ID NO:13 or SEQID NO:14. In some embodiments, the bacterial species is a *Methylobacterium* species.

In a second aspect, the present invention provides an artificially formulated inoculant comprising at least one biologically pure culture of a bacterial species selected from the *Enterobacter, Methylobacterium, Sphingomonas*, and *Pleomorphomonas* genera as described herein. In one embodiment, the inoculant comprises a mixture of at least two biologically pure cultures of these bacterial species. In some embodiments, the preparation of the inoculant comprises large-scale production of the bacterial species described herein in a medium, optionally dehydrated in a suitable manner that maintains cell viability and the ability to artificially inoculate and colonize host plants. In some embodiments, the inoculant is optionally supplemented with trace metal ions. In one embodiment, the trace metal ions are selected from the group consisting of molybdenum ($Mo^{2+}$) ions, iron ($Fe^{2+}$) ions, manganese ($Mn^{2+}$) ions, or any combination of these ions. In another embodiment, the concentration of the trace metal ions in the inoculant is between about 0.1 mM and about 50 mM. In some embodiments, the inoculant is formulated with a carrier. Any suitable carrier can be used and examples of suitable carriers include, but are not limited to, beta-glucan, carboxylmethyl cellulose (CMC), bacterial EPS, sugar and animal milk. In some embodiments, bacterial species that can be used for the inoculants of the present invention are those bacterial species described herein. In other embodiments, bacterial species that can be used for the inoculants of the present invention can be isolated by culturing a plant tissue extract or leaf surface wash in a medium with no added nitrogen source or sourced from a microbial collection centre based on taxonomy classifications and the characteristics of the bacterial species described herein. In some embodiments, the inoculant is effective in promoting plant growth, maintaining high chlorophyll content in leaves, increasing fruit or seed numbers, increasing fruit or seed unit weight and reducing $NO_2$ emission due to reduced nitrogen fertilizer usage. In other embodiments, these properties are evidenced in plant species of the genera *Jatropha, Sorghum, Gossypium, Elaeis, Oryza, Ricinus* and *Manihot*.

In a third aspect, the present invention provides a method for promoting plant productivity in a non-legume plant species. In some embodiments, the plant productivity is plant growth, maintenance of high chlorophyll content in leaves, increasing fruit or seed numbers, increasing fruit or seed unit weight or any combination of these characteristics. In other embodiments, plant productivity is also a reduction in $NO_2$ emission which results from reduced nitrogen fertilizer use. In some embodiments, the non-legume plant species is selected from species of the genera *Jatropha, Sorghum, Gossypium, Elaeis, Ricinus, Oryza* and *Manihot*. In accordance with the present invention, the method comprises inoculating plants with a bacterial inoculant described herein. In one embodiment, the inoculant is sprayed on the plant aerial parts. In another embodiment, the inoculant is applied to the roots by inserting into furrows in which the plant seeds are planted, watering to the soil or dipping the roots in a suspension of the inoculant. In an additional embodiment, the inoculant is applied as a seed coating. In some embodiments, the inoculant comprises the trace metal ions described herein.

In other embodiments, the plant is sprayed with a trace metal ion solution that contains the trace metal ions described herein in addition to an inoculant which may not contain the trace metal ions.

BRIEF DESCRIPTION OF THE FIGURES

FIG. 6a: Strain R5-392$^T$ grown in N-free medium and growth was recorded as $OD_{600\ nm}$ at different time intervals. For measurement of nitrogenase activity, grown on N-free liquid cultures by injecting purified 15% acetylene (v/v) and incubate at 30° C. and then analyzed for ethylene production by GC. FIG. 6b: Nitrogenase switch-off by ammonium ions (top panel) and response to addition of nitrogenase cofactor Fe and Mo (bottom panel) in *Pleomorphomonas jatrophae* strain R5-392.

DETAILED DESCRIPTION OF THE INVENTION

Figure 1:
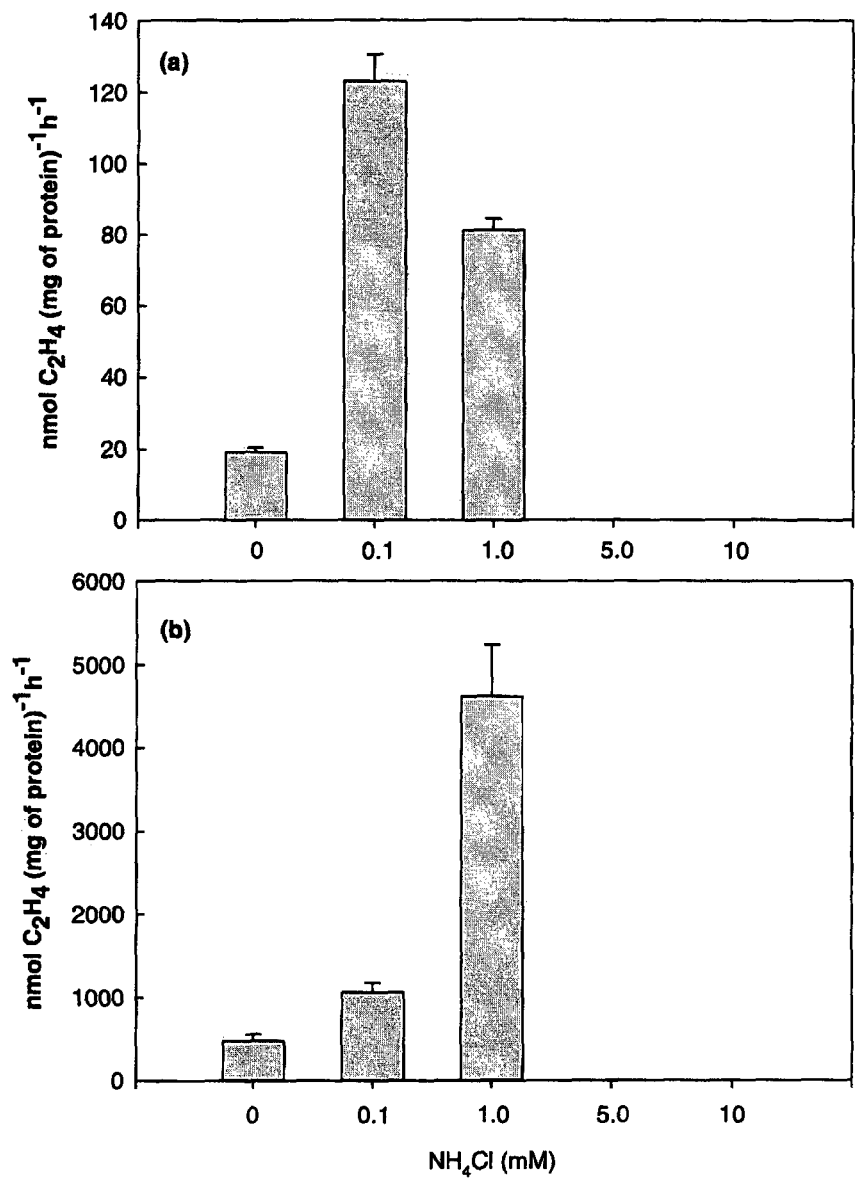
FIGS. 1a and 1b show the effect of ammonium chloride addition on nitrogenase activity of *Methylobacterium* sp. strain. L2-4 (FIG. 1a) and *Enterobacter* sp. strain R4-368 (FIG. 1b). Nitrogenase activity was measured for cultures grown in 125-ml serum bottles containing N-free medium supplemented with different levels of ammonium chloride at 30° C. for 48 h. Error bars indicate ±SD.

The present invention relates to novel clean technologies for agriculture and environment managements. In particular, the practice of this invention leads to reduced dependence on chemical nitrogen fertilizer; faster plant growth; improves crop productivity and reduced greenhouse gas $NO_2$ emission in agriculture. In some embodiments, the present invention relates to methods of reducing chemical fertilizer usage and greenhouse gas nitrous oxide emission and to methods of improving plant growth rate and seed productivity in agriculture through the application of a novel artificially manufactured formula containing a nitrogen-fixing bacterium that efficiently colonizes non-legume plants in aerial parts and root system. The bacteria inocula and methods are particularly suitable for plants in the genera *Jatropha, Sorghum, Gossypium, Elaeis, Otyza, Ricinus* and *Manihot*.

As used herein "bacterial inoculant," "inoculant" or "inoculum" refers to a preparation that includes one or more bacterial species described herein.

The term "biologically pure culture" or "substantially pure culture" shall be deemed to include a culture of a bacterial species described herein containing no other bacterial species in quantities sufficient to interfere with the replication of the culture or be detected by normal bacteriological techniques.

The term "plant productivity" refers generally to any aspect of growth or development of a plant that is a reason for which the plant is grown. For example, when referring to food crops, such as grains or vegetables, crop productivity generally refers to the yield of grain or fruit, etc., harvested from a particular crop. Thus, for purposes of the present invention, improved plant productivity refers broadly to improvements in yield of grain, fruit, flowers, or other plant parts harvested for various purposes, improvements in growth of plant parts, including stems, leaves and roots, promotion of plant growth, maintenance of high chlorophyll content in leaves, increasing fruit or seed numbers, increasing fruit or seed unit weight, reducing $NO_2$ emission due to reduced nitrogen fertilizer usage and similar improvements of the growth and development of plants.

In a first aspect, the present invention provides a biologically pure culture of a bacterial species selected from the *Enterobacter, Methylobacterium, Sphingomonas*, and *Pleomorphomonas* genera as described herein. In some embodiments, the bacterial species of the present invention are able to efficiently reduce atmospheric $N_2$ to ammonia as evidenced by the AR assay in planta. In some embodiments, the $N_2$ reduction occurs on the leaf surface. In other embodiments, the $N_2$ reduction occurs inside the leaf surface. In additional embodiments, the $N_2$ reduction occurs on the surface of the roots or root system. In further embodiments, the $N_2$ reduction occurs inside the root tissue. In some embodiments, the bacterial species is able to self-propagate efficiently on the leaf surface, root surface or inside plant tissues without inducing a noticeable plant defense reaction, such as cell death. In other embodiments, bacterial species of the present invention can be isolated by culturing a plant tissue extract or leaf surface wash in a medium with no added nitrogen source, using suitable methods such as those described herein or similar methods well known to the skilled artisan or obvious modifications thereof.

In one embodiment, the genomic DNA of the bacterial species shares least 97% and preferably at least 98% identity to SEQ ID NO:10. In some embodiments, the bacterial species is an *Enterobacter* species containing a set of genes required for nitrogen-fixation. In some embodiments, the *Enterobacter* species produces substantial amounts of EPS, or endoglucanase. In another embodiment, the genomic DNA of the bacterial species shares 97% and preferably at least 98% identity to SEQ ID NO:11. In some embodiments, the bacterial species is a *Pleomorphomonas* species in which the nitrogen-fixing capability is stimulated by about 0.1 mM to about 0.5 mM of $NH_4^+$ ion. In an additional embodiment, the genomic DNA of the bacterial species shares 97% and preferably at least 98% identity homology to SEQ ID NO:12. In some embodiments, the bacterial species is a *Sphingomonas* species that is able to grow in nitrogen-free medium. In a further embodiment, the genomic DNA of the bacterial species shares 97% and preferably at least 98% identity to SEQ ID NO:13 or SEQID NO:14. In some embodiments, the bacterial species is a *Methylobacterium* species.

A biologically pure culture of *Enterobacter* species R4-368 and *Pleomorphomonas jatrophae* R5-392 were deposited on Jan. 6, 2012 under terms of the Budapest Treaty with the AGRICULTURAL RESEARCH SERVICE CULTURE COLLECTION (NRRL) (International Depositary Authority), National Center for Agricultural Utilization Research Agricultural Research Service, U.S. Department of Agriculture, 1815 North University Street, Peoria, Ill. 61604 U.S.A., and assigned Accession Number NRRL B-50631 and NRRL B-50630, respectively. These strains can be cultured in $R_2A$ medium (Yeast extract 0.5 g/l; Proteose Peptone 0.5 g/l; Casamino acids 0.5 g/l; Glucose 0.5 g/l; Soluble starch 0.5 g/l; Na-pyruvate 0.3 g/l; $K_2HPO_4$ 0.3 g/l; $MgSO_4*7H_2O$ 0.05 g/l; agar 15 g/l; pH7.2).

A biologically pure culture of *Methylobacterium* sp. L2-4; *Methylobacterium* sp. L2-76 and *Sphingomonas* sp. S6-274 were deposited on Jan. 6, 2012 under terms of the Budapest Treaty with the AGRICULTURAL RESEARCH SERVICE CULTURE COLLECTION (NRRL) (International Depositary Authority), National Center for Agricultural Utilization Research Agricultural Research Service, U.S. Department of Agriculture 1815 North University Street, Peoria, Ill. 61604 U.S.A., and assigned Accession Number NRRL B-50628, NRRL B-50629 and NRRL B-50632, respectively. These strains can be cultured in 869 medium (Tryptone 10.0 g/l; Yeast extract 5.0 g/l; NaCl 5.0 g/l; D-glucose 1.0 g/l; $CaCl_2.2H_2O$ 0.345 g/l; pH 7.0).

It is anticipated that certain mutants of the bacterial species described herein may also enhance plant growth comparable to the non-mutated forms. Mutants of the bacterial species described herein may include both naturally occurring and artificially induced mutants. Certain of these mutants will be found to useful using the assays described herein. Others mutants may be induced by subjecting the bacterial species described herein to known mutagens, such as N-methyl-nitrosoguanidine, using conventional methods. See, for example, U.S. Pat. No. 4,877,738 and U.S. Pat. No. 5,552,138, each incorporated herein by reference.

In a second aspect, the present invention provides an artificially formulated inoculant comprising at least one biologically pure culture of a bacterial species selected from the *Enterobacter*, *Methylobacterium*, *Sphingomonas*, and *Pleomorphomonas* genera as described herein. In one embodiment, the inoculant comprises a mixture of at least two biologically pure cultures of these bacterial species. In some embodiments, the preparation of the inoculant comprises large-scale production of the bacterial species described herein in a medium, optionally dehydrated in a suitable manner that maintains cell viability and the ability to artificially inoculate and colonize host plants. In some embodiments, the concentration of bacterial species in the inoculant is $10^8$ to $10^{10}$ CFU/ml. In some embodiments, the inoculant is optionally supplemented with trace metal ions. In one embodiment, the trace metal ions are selected from the group consisting of molybdenum ($Mo^{2+}$) ions, iron ($Fe^{2+}$) ions, manganese ($Mn^{2+}$) ions, or any combination of these ions. In another embodiment, the concentration of the trace metal ions in the inoculant is between about 0.1 mM and about 50 mM.

In some embodiments, the inoculant is formulated with a carrier. Any suitable carrier can be used. Examples of suitable carriers include, but are not limited to, beta-glucan, CMC, bacterial EPS, sugar and animal milk. Alternatively, peat or planting materials can be used as a carrier. In addition, biopolymers can be used as a carrier in which the inoculant is entrapped in the biopolymer. See, for example, U.S. Pat. Nos. 4,828,600, 5,061,490, 5,951,978 and No. 7,393,678, each incorporated herein by reference.

In some embodiments, bacterial species that can be used for the inoculants of the present invention are those bacterial species described herein. In other embodiments, bacterial species that can be used for the inoculants of the present invention can be isolated by culturing a plant tissue extract or leaf surface wash in a medium with no added nitrogen source or sourced from a microbial collection centre based on taxonomy classifications and the characteristics of the bacterial species described herein. In some embodiments, the inoculant is effective in promoting plant growth, maintaining high chlorophyll content in leaves, increasing fruit or seed numbers, increasing fruit or seed unit weight and reducing $NO_2$ emission due to reduced nitrogen fertilizer usage. In other embodiments, these properties are evidenced in plant species of the genera *Jatropha*, *Sorghum*, *Gossypium*, *Elaeis*, *Ricinus*, *Oryza* and *Manihot*.

In a third aspect, the present invention provides a method for promoting plant productivity in a non-legume plant species. In some embodiments, the plant productivity is plant growth, maintenance of high chlorophyll content in leaves, increasing fruit or seed numbers, increasing fruit or seed unit weight or any combination of these characteristics. In other embodiments, plant productivity is also a reduction in $NO_2$ emission which results from reduced nitrogen fertilizer use. In some embodiments, the non-legume plant species is selected from species of the genera *Jatropha*, *Sorghum*, *Gossypium*, *Elaeis*, *Ricinus*, *Oryza* and *Manihot*. In accordance with the present invention, the method comprises inoculating plants with a bacterial inoculant described herein. In one embodiment, the inoculant is sprayed on the plant aerial parts. In another embodiment, the inoculant is applied to the roots by inserting into furrows in which the plant seeds are planted, watering the soil or dipping the roots in a suspension of the inoculant. In an additional embodiment, the inoculant is applied as a seed coating. In some embodiments, the inoculant comprises the trace metal ions described herein. In other embodiments, the plant is sprayed with a trace metal ion solution that contains the trace metal ions described herein in addition to an inoculant which may not contain the trace metal ions.

In one embodiment, the bacterial inoculant can be applied to plant seeds through the use of a suitable coating mechanism or binder prior to the seeds being sold into commerce for planting. The process of coating seed with such an inoculum is generally well known to the skilled artisan. For example, the bacterial species described herein may be mixed with a porous, chemically inert granular carrier, such as described by U.S. Pat. No. 4,875,921, incorporated herein by reference. In another embodiment, the bacterial inoculant may be prepared with or without a carrier and sold as a separate inoculant to be used directly by the grower, such as by inserting directly into the furrows into which the seed is planted or by spraying the plant leaves. The process for inserting such inoculants directly into the furrows during seed planting is also generally well known to the skilled artisan, as is spraying the plants with the bacterial inoculant.

In general, the density of inoculation of the bacterial species onto seed, into furrows, or wetted on roots should be sufficient to populate the sub-soil region adjacent to the roots of the plant with viable bacterial growth. Similarly, the density of inoculation of the bacterial species sprayed onto plants should be sufficient to populate the leaves of the plant with viable bacterial growth. An effective amount of bacterial inoculant should be used. An effective amount is that amount sufficient to establish sufficient bacterial growth so that the plant productivity is improved.

It will be appreciated by the skilled artisan that a bacterial inoculant of the type described herein offers several significant potential advantages over the chemical inoculants or growth hormones or similar agents commonly used in agriculture today. By the very nature of the bacterial inoculant, the bacterial species are self-sustaining in a continuous fashion once the plants have been inoculated by any of the methods described herein. Therefore, there is no need for retreatment of the plants during the crop season. The bacterium grows in cultivation along with the plants and should continue to exhibit its beneficial effect on the plant throughout the agricultural season. This is in strong contrast to chemical growth agents or fungicides which must be retreated periodically to have a continuing effect on inhibition of the fungus in question or to help improve the plant growth throughout its life cycle. Since the bacterial inoculant of the present invention can be inoculated onto the seeds using a dry or wet formulation, the application of this technique is relatively simple to the farmer since the seeds can be inoculated prior to distribution. Since the bacterial inoculant of the present invention can be sprayed onto plants, the application of this technique is relatively simple to the farmer. In these ways, a significant economic advantage is achievable.

The practice of the present invention employs, unless otherwise indicated, conventional techniques of chemistry, molecular biology, microbiology, recombinant DNA, genetics, immunology, cell biology, cell culture and transgenic biology, which are within the skill of the art. See, e.g., Maniatis et al., 1982, *Molecular Cloning* (Cold Spring Harbor Laboratory Press, Cold Spring Harbor, N.Y.; Sambrook et al., 1989, *Molecular Cloning*, 2nd Ed. (Cold Spring Harbor Laboratory Press, Cold Spring Harbor, N.Y.); Sambrook and Russell, 2001, *Molecular Cloning*, 3rd Ed. (Cold Spring Harbor Laboratory Press, Cold Spring Harbor, N.Y.); Ausubel et al., 1992), *Current Protocols in Molecular Biology* (John Wiley & Sons, including periodic updates); Glover, 1985, *DNA Cloning* (IRL Press, Oxford); Russell, 1984, *Molecular biology of plants: a laboratory course manual* (Cold Spring Harbor Laboratory Press, Cold Spring Harbor, N.Y.); Anand, *Techniques for the Analysis of Complex Genomes*, (Academic Press, New York, 1992); Guthrie and Fink, *Guide to Yeast Genetics and Molecular Biology* (Academic Press, New York, 1991); Harlow and Lane, 1988, *Antibodies*, (Cold Spring Harbor Laboratory Press, Cold Spring Harbor, N.Y.); *Nucleic Acid Hybridization* (B. D. Hames & S. J. Higgins eds. 1984); *Transcription And Translation* (B. D. Hames & S. J. Higgins eds. 1984); *Culture Of Animal Cells* (R. I. Freshney, Alan R. Liss, Inc., 1987); *Immobilized Cells And Enzymes* (IRL Press, 1986); B. Perbal, *A Practical Guide To Molecular Cloning* (1984); the treatise, *Methods In Enzymology* (Academic Press, Inc., N.Y.); *Methods In Enzymology*, Vols. 154 and 155 (Wu et al. eds.), *Immunochemical Methods In Cell And Molecular Biology* (Mayer and Walker, eds., Academic Press, London, 1987); *Handbook Of Experimental Immunology*, Volumes I-IV (D. M. Weir and C. C. Blackwell, eds., 1986); Riott, *Essential Immunology*, 6th Edition, Blackwell Scientific Publications, Oxford, 1988; Fire et al., *RNA Interference Technology: From Basic Science to Drug Development*, Cambridge University Press, Cambridge, 2005; Schepers, *RNA Interference in Practice*, Wiley-VCH, 2005; Engelke, *RNA Interference (RNAi): The Nuts & Bolts of siRNA Technology*, DNA Press, 2003; Gott, *RNA Interference, Editing, and Modification: Methods and Protocols (Methods in Molecular Biology)*, Human Press, Totowa, N.J., 2004; Sohail, *Gene Silencing by RNA Interference: Technology and Application*, CRC, 2004.

EXAMPLES

The present invention is described by reference to the following Examples, which is offered by way of illustration and is not intended to limit the invention in any manner. Standard techniques well known in the art or the techniques specifically described below were utilized.

Example 1

Isolation of Diazotrophic Endophytes

*Jatropha* (*Jatropha curcas* L.) cultivars were sampled from the research plots of Agrotechnology Experimental Station located at Lim Chu Kang, Singapore. Plants were sampled from three trees of different cultivars that included origin from Indonesia, China and India. The root samples (~1.2-2 cm dia) with adhering soil were carefully removed from root with a trowel and collected in sterile plastic bags. Stem cuttings (~1.5 to 2.5 cm diameter) were removed from the plants with clippers and matured third leaves (non-pathogenic) from healthy branches that were placed on ice for shipment from the field to laboratory and processed immediately. Root, stem cuttings (~50 g) and leaf (~15-20 g) samples were thoroughly washed in distilled water, surface sterilized for 1 min in 90% ethanol followed by 10 min in 15% $H_2O_2$ and rinsed 3-5 times in sterile distilled water. A 100-μl sample of the water from the third rinse was plated on rich medium to verify the efficiency of sterilization. After sterilization, the roots and shoots were macerated in 10 ml 10 mM $MgSO_4$ using a blender under sterile conditions. Serial dilutions were made, and 100-μl samples were plated on non-selective media in order to test for the presence of the endophytes and their characteristics. The bacteria were isolated from spread plate technique (100-μl) using different media with agar/phytagel such as N-free media (Nfb) (Baldani et al., 1980) for diazotrophs, rich media (M869) (Barac et al., 2004); for total heterotrophs and minimal medium (AMS) (Whittenbury et al., 1970); for methylotrophic bacteria. For isolation of diazotrophs, the suspension ($10^{-1}$ to $10^{-5}$) were placed in duplicate tubes containing semi-solid N-free media and incubated for 96 h at 30° C. Growth pellicles in semi-solid media were streaked on to N-free agar media for single colony preservation and for further use.

Example 2

Bacterial Inoculants and Culture Conditions

*Methylobacterium* strains were grown in liquid medium 869 (Barac et al., 2004) with 1% methanol as the carbon source. Root isolates were cultivated in liquid medium 869 or 2xYT without methanol. All cultures were incubated at 30° C. and grown until early stationary phase. Just before inoculation, cells were harvested (10000 rpm, 8 min), washed once and resuspended in SDW or 10 mM $MgSO_4$ solution, the optical density at 600 nm ($OD_{600\ nm}$) was adjusted, and inoculated as follows: for root inoculation, equal volume of cell suspension ($OD_{600\ nm}$=1.0 or $10^8$ cfu $ml^{-1}$) of each isolate was mixed and added at the time of sowing and at 15 days after sowing (DAS); for leaf inoculation, mixed or individual isolate was given as foliar spray till the wetting of leaves at 15 and 30 DAS (volume varied depending on the plant size and leaf number).

Example 3 nifH Amplification and Sequencing

The presence of the nifH gene was determined by a PCR as described by Pinto-Tomás et al. (2009). To amplify nifH gene using universal primers nif-Fo (5'-AAA GGY GGW ATC GGY AAR TCC ACC AC-3'; SEQ ID NO:1) and nif-Re (5'-TTG TTS GCS GCR TAC ATS GCC ATC AT-3'; SEQ ID NO:2) using the stringent PCR conditions described by Widmer et al. (1999) in order to reduce the emergence of falsely positive amplifications, including the following cycling conditions: 95° C./5min, 40 cycles of 94° C./15 s, 92° C./15 s, 54° C./8 s, 56° C./30 s, 74° C./10 s and 72° C./10 s, and final extension for 10 min/72° C. PCR products were eluted with QIAquick gel extraction kit prior to preparing sequencing reactions with the BigDye reaction mix and loaded into an Applied Biosystems 3700 automated DNA sequencing instrument. inFH sequences from this study and close reference sequences obtained from the NCBI database by BLAST analysis.

Example 4

Nitrogenase Assays In Vitro

The acetylene-reduction (AR) assay was performed on free-living cultures as well as on cultures in association with crop plants. Nitrogen-fixing ability was determined by growing strains in 40 ml nitrogen-free medium (DSMZ medium no. 3) contained in a 125 ml serum bottle (Wheaton Industries Inc., USA). The medium contained the following (in 1 l distilled water): 5.0 g glucose, 5.0 g mannitol, 0.1 g $CaCl_2.2H_2O$, 0.1 g $MgSO_4.7H_2O$, 5.0 mg $Na_2MoO_4.2H_2O$, 0.9 g $K_2HPO_4$, 0.1 g $KH_2PO_4$, 0.01 g $FeSO_4.7H_2O$, 5.0 g $CaCO_3$ and 1 ml trace element mixture. The trace element mixture (SL-6, in DSMZ medium no. 27) contained the following ($l^{-1}$ distilled water): 0.1 g $ZnSO_4.7H_2O$, 0.03 g $MnCl_2.4H_2O$, 0.3 g $H_3BO_3$, 0.2 g $CoCl_2.6H_2O$, 0.01 g $CuCl_2.2H_2O$ and 0.02 g $NiCl_2.6H_2O$. Acetylene reduction was performed for all liquid cultures by injecting purified acetylene into appropriate containers sealed with gas-tight serum stoppers to yield 15% acetylene (v/v); this was followed by incubation for up to 96 h at 30° C. At intervals gas samples (0.5 ml) were removed by PTFE-syringe (Hewlett-Packard, USA) and analysed by Gas Chromatograph (GC 6890N, Agilent Technologies Inc., USA) with an flame ionization detector operated as follows: carrier gas, He; 35 ml/min; detector temperature, 200° C.; column, GS-Alumina (30 m×033 mm I.D.); pressure, 4.0 psi. Standard curve was prepared with ethylene ($C_2H_4$, Product Number: 00489, Sigma-Aldrich) injected in duplicate, the concentration ranged from 1 to 1000 n moles and calibrated (peak height vs nmol of $C_2H_4$). The protein concentration was determined by a modified Lowry method with bovine serum albumin as standard.

Example 5

Nitrogenase Assay in Planta

Acetylene-reduction (AR) assay was performed 2-3 weeks after inoculation, and the viable bacterial counts on shoot/roots were determined by serial dilution technique. Samples from each replication were collected from the glass house and most of the adhering soil was removed by shaking. Shoot/root/entire seedlings were inserted into the 125 ml glass bottles, closed with a 20 mm red stopper sleeve. After removing an equivalent volume of air, acetylene was injected into these bottles to give a final concentration of 15% and incubated at 30° C. for 4-12 h. Gas Chromatograph operating conditions was described by earlier. All values expressed were obtained after deducting the ethylene values for a blank treatment without samples.

Example 6

Enumeration of Bacterial Populations

Triplicate plant samples were randomly picked on each sampling, and each replicate consists of root and aerial parts from three plants. For all bacterial enumerations, the homogenates were serially diluted using sterile distilled water and plated on to AMS media with 0.5% methanol to determine the *Methylobacterium* population or to M869 plates for total bacterial population. Bacterial colonies were counted after incubating the plates for 5 days at 30° C.

Example 7

In Vitro and in Planta AR Activity of Selected Diazotrophic Isolates

Many diazotrophic species were isolated from jatropha plant or rhizophere. The nitrogen-fixing capability was confirmed by the presence of nifH-like gene by PCR, AR activity in vitro and in planta. We found that nitrogenase activity in isolate bacteria culture is significantly different from their performance observed in planta. Table 1 lists the activity of selected strains.

TABLE 1

AR Activity of Selected Diazotrophic Isolates

| Selected strains | Medium used | Nitrogenase activity in pure culture (nmol $C_2H_4$ $h^{-1}$ mg $protein^{-1}$) | In planta AR activity (nmol $C_2H_4$ $h^{-1}$ $plant^{-1}$) | nifH gene* | Endoglucanase Activity |
|---|---|---|---|---|---|
| *Methylobacterium* sp. L2-4 | JNFb | 661.3 ± 65.31 | 94.17 ± 9.52 | +(420 nt) | + |
| *Methylobacterium* sp. L2-76 | JNFb | 272.2 ± 20.15 | 32.70 ± 5.21 | + | + |
| *Methylobacterium* sp. L7-515 | JNFb | 223.3 ± 32.14 | 61.57 ± 7.62 | + | + |

TABLE 1-continued

AR Activity of Selected Diazotrophic Isolates

| Selected strains | Medium used | Nitrogenase activity in pure culture (nmol $C_2H_4$ $h^{-1}$ mg protein$^{-1}$) | In planta AR activity (nmol $C_2H_4$ $h^{-1}$ plant$^{-1}$) | nifH gene* | Endoglucanase Activity |
|---|---|---|---|---|---|
| *Enterobacter* sp0 R4-368 | DSMZ** | 1060.7 ± 110.6 | 220.08 ± 20.08 | +(432 nt) | + |
| *Enterobacter* sp. R5-362 | DSMZ | 960.5 ± 110.5 | 77.54 ± 8.54 | + | + |
| *Enterobacter* sp. R4-390 | DSMZ | 1012.8 ± 62.8 | 71.13 ± 10.07 | + | + |
| *Pleomorphomonas jatrophae* R5-392 | DSMZ | 92.79 ± 4.8 | Nd | +(409 nt) | − |
| *Sphingomonas* sp. S6-274 | DSMZ | 16.14 ± 1.2 | Nd | + | + |

Note:
*nifH gene - amplified using PCR and the products are sequenced for further confirmation.
**DSMZ N-free medium no. 3; Acetylene reduction was performed for all liquid cultures by injecting purified acetylene into appropriate containers sealed with gastight serum stoppers to yield 15% acetylene (v/v); this was followed by incubation for up to 96 h at 30° C. Ethylene peak is not detected in control bottle without addition of 15% acetylene (v/v) into the headspace. Each value is the mean ± SD of three replications per treatment.
Nd: not determined.

Example 8

Effect of Ammonium Ion on Nitrogen-Fixing Activity

Resistance to ammonia is a critical feature of nitrogen-fixing bacteria inoculants for this invention. To demonstrate this, we assay the AR activity of two best candidates of our inoculants under the conditions with various concentration of $NH_4Cl$. Surprisingly, both *Enterobacter* sp. R4-368 and *Methylobacterium* sp. L2-4 showed not only strong activity up to 1 mM but also significantly enhanced activity by the $NR_4^+$ ion although inhibitory effect was observed at about 5 mM (FIGS. 1a and 1b).

Example 9

Effect of Metal Ions on N-Fixation

Figure 2:
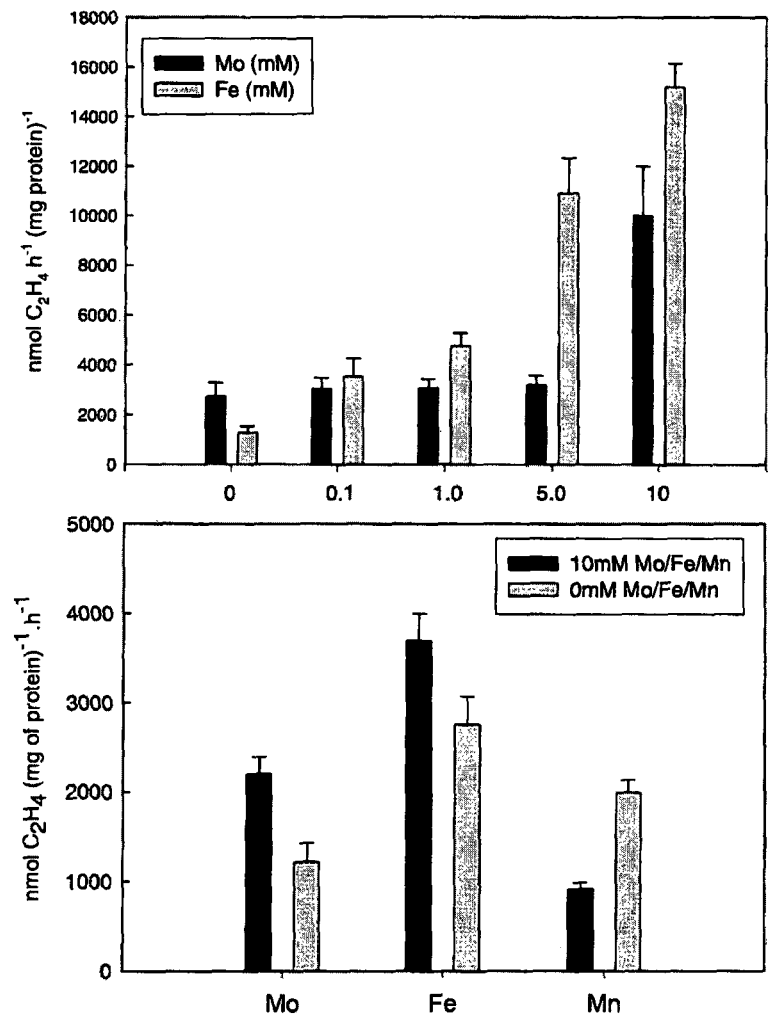
FIG. 2 shows the effect of nitrogenase cofactor (Mo/Fe/Mn) addition on nitrogenase activity of *Enterobacter* sp. strain R4-368 (top) and *Methylobacterium* sp. strain L2-4 (bottom). Nitrogenase activity was measured for cultures grown in 125-ml serum bottles containing N-free medium supplemented with different levels of Mo/Fe/Mn at 30° C. for 48 h.
Figure 3:
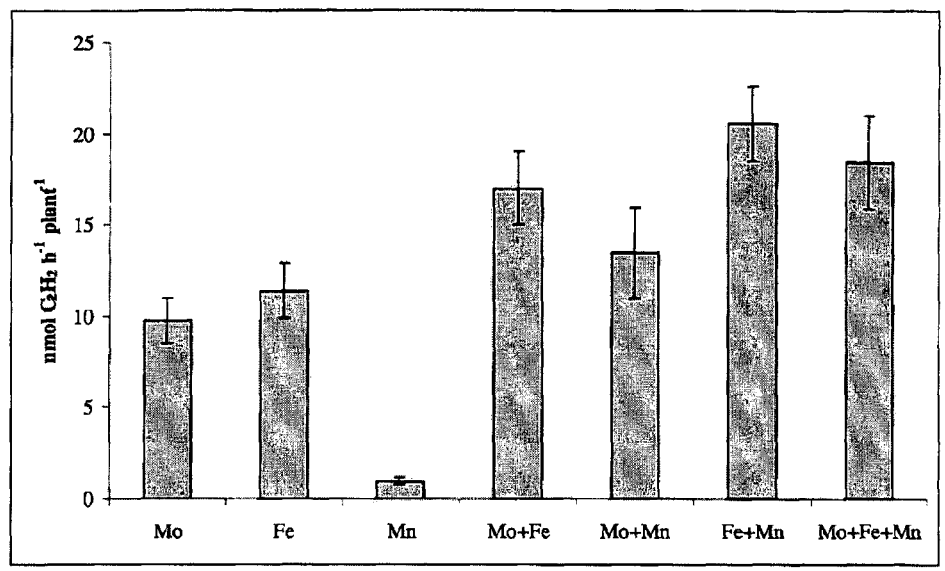
FIG. 3 shows the nitrogen-fixing activity in Jatropha of selected nitrogen-fixing strains in the presence of essential metals (Mo/Fe/Mn). Ethylene emission from Jatropha seedlings added with 15% acetylene (v/v) into the headspace was determined with and without inoculation of N-fixing root isolates. Acetylene reduction activity was calculated from the difference between inoculated with and without N-fixing root isolates. Values given are the means±standard deviations for triplicate determinations.

We assayed nitrogenase activity in media supplemented $Na_2MoO_4$ or $FeSO_4 7H_2O$ at various concentrations (0, 0.1, 0.5, 1, 10 mM) in N-free medium. Nitrogenase activity was clearly stimulated by $Fe^{2+}$ and molybdenum ($Mo^{2+}$) ions (FIGS. 2 and 3).

Example 10

Agronomical Performance of *Jatropha curcas* Inoculated with N-Fixing Strains

To confirm the efficacy of nitrogen-fixing bacterial inoculants in plants, selected strains were inoculated to *Jatropha curcas* seedlings either in a single isolates or mix isolates. Plants were grown in the open air in plastic pots (30 cm in diameter) after bacterial inoculation. From the time of flowering to harvesting, commercial NPK fertilizers was applied at half of the recommended dose (0.5 g/plant) once in 15 days intervals. As shown in Table 4, significant improvements in chlorophyll content, leaf AR activity, seed yield and single seed weight were observed. Noticeably, mixed inoculation of root and leaf isolates lead to best chlorophyll content and AR activity. Flowering time was also shortened, particularly in treatments with L2-4 strains. The relatively high AR activity in control plants may result from naturally occurring N-fixing species from the environment. Importantly, total seed yields were increased to about 4-fold when inoculated with a single leaf isolate L2-4 or mix root isolates (Table 2).

TABLE 2

Effect of N-Fixing Strains on *Jatropha curcas*

| Treatments | Relative Chlorophyll content | AR-activity (nmol $C_2H_4$ $h^{-1}$ g leaf$^1$) | Average time to flowering (DAP) | No. of fruits per treatment | Number of seeds/plant | Total seed weight per treatment (g) | Single seed weight (g) |
|---|---|---|---|---|---|---|---|
| Control | 33.29 ± 2.44 | 18.11 ± 2.1 | 137 | 26 ± 2.87 | 75 ± 8.14 | 36.25 | 0.483 |
| L2-4 | 38.17 ± 4.10 | 22.31 ± 3.3 | 110 | 101 ± 7.91 | 261 ± 20.78 | 134.89 | 0.517 |
| L2-76 | 36.47 ± 4.01 | 20.95 ± 4.0 | 125 | 58 ± 4.37 | 157 ± 11.41 | 81.56 | 0.519 |
| Leaf isolates (LI) | 37.66 ± 4.17 | 24.00 ± 4.0 | 118 | 43 ± 2.72 | 119 ± 8.13 | 62.63 | 0.526 |
| Root isolates (RI) | 38.12 ± 3.30 | 19.97 ± 2.0 | 124 | 98 ± 9.00 | 286 ± 25.47 | 145.27 | 0.508 |

TABLE 2-continued

Effect of N-Fixing Strains on *Jatropha curcas*

| Treatments | Relative Chlorophyll content | AR-activity (nmol $C_2H_4$ $h^{-1}$ g $leaf^1$) | Average time to flowering (DAP) | No. of fruits per treatment | Number of seeds/plant | Total seed weight per treatment (g) | Single seed weight (g) |
|---|---|---|---|---|---|---|---|
| RI + LI (MI) | 40.07 ± 5.14 | 36.67 ± 5.7 | 115 | 73 ± 5.03 | 182 ± 12.41 | 92.05 | 0.506 |

Note:
Each value is the mean ± SD of eight replications (n = 8). Leaf isolates (LI): L2-4 (*Methylobacterium* sp.), L2-76 (*Methylobacterium* sp.) and S6-274 (*Sphingomonas* sp.); Root isolates (RI): R4-368 (*Enterobacter* sp.), R5-362 (*Enterobacter* sp.), R5-431 (*Klebsiella* sp.), R7-601 (*Sinorhizobium* sp.) and R1-99 (*Rhizobium* sp.). For treatments that include leaf isolates, the cultures were applied using a hand sprayer (25 ml per pot; 1 × 10$^9$ CPU ml$^{-1}$ of culture or wetting of all the leaves) at 30 and 90 days after planting (DAP). Chlorophyll content and AR-activity measured on 30 days after inoculation (DAI). Mature fruits were collected continuously and dried at 37° C. for 2 days. Seeds were collected from dried fruits and stored in 4° C. for further analysis. Fruit and seed yield data was recorded over a period of 7 months.

To demonstrate that the bacteria species are able to self-propagate in plant tissues, non-surface sterilized homogenates were serially diluted using sterile distilled water and MIN techniques were performed with 3 tubes containing Nfb media using from $10^{-3}$ to $10^{-5}$ dilutions and incubated at 30° C. for 7 days. For endophytic population before homogenization, leaf and root tissues were surface-sterilized by immersion in 70% ethanol, 1 min; 15% $H_2O_2$ for 1 min followed by 5-10 thorough rinsing in sterile distilled water. Serial dilutions were also plated on agar N-free media. Bacterial colonies were counted after incubating the plates for 5 days at 30° C. Results are shown in Table 3. For heterotrophic and methlotrophic population were showed the same trend as higher population of leaf associated bacteria than endophytic populations (data not shown).

TABLE 3

Diazotrophic Bacterial Populations (MPN Techniques)

| | Population (Log cfu/g sample) | | | |
|---|---|---|---|---|
| | Leaf sample | | Root sample | |
| Treatments | Leaf associated | Endophytic | Root associated | Endophytic |
| Control | 3.97 ± 0.97 | 2.48 ± 0.18 | 2.56 ± 0.16 | 2.46 ± 0.36 |
| L2-4 | 5.38 ± 0.38 | 2.96 ± 0.46 | 3.51 ± 0.41 | 2.81 ± 0.11 |
| L2-76 | 5.61 ± 0.51 | 2.82 ± 0.72 | 3.16 ± 0.36 | 2.64 ± 0.34 |
| Leaf isolates (LI) | 5.46 ± 0.26 | 3.10 ± 0.30 | 3.24 ± 0.54 | 2.59 ± 0.19 |
| Root isolates (RI) | 4.12 ± 0.12 | 3.05 ± 0.25 | 4.32 ± 0.32 | 3.65 ± 0.25 |
| RI + LI (MI) | 5.72 ± 0.62 | 3.21 ± 0.31 | 4.66 ± 0.66 | 3.88 ± 0.43 |

Note:
Leaf associated or endophytic populations from both surface and non-surface sterilized leaves were measured in Nfb media at the time of fruit harvesting stage i.e. 6 months after $2^{nd}$ inoculations.

Example 11

Promotion of *Jatropha* Seedling Growth

*Jatropha* (cv. MD44) seeds were surface sterilized by immersion in 70% ethanol, 1 min; 2% NaOCl for 30 sec followed by 5-10 thorough rinsing in sterile distilled water. For plant inoculation experiments, *Methylobacterium* strains (leaf isolates, L2-4 and L7-515) were grown in liquid 2xYT medium (root isolates R4-368, R5-362, R5-431, R7-601 and R1-99 were grown in without methanol) containing methanol (30 mM) to midexponential growth phase, centrifuged, washed, resuspended in sterile distilled water and stored in 4° C. until use. The bacteria were adjusted to an $OD_{600\ nm}$ of 1.2 ($10^8$ cfu per ml) and used for plant inoculation after sterilization of *Jatropha* seeds. For mixed inoculation, equal volumes of five cultures were mixed and then used for seed imbibition (in RT at 6 h for 60 rpm), root application (2 ml per pot after sowing) and phyllosphere spray till wetting of leaves.

Under glass house growth conditions, the analysis that was carried out at 45 DAS showed that for most of the plant parameters examined, there was a significant increase in N-fixing bacteria-treated plants compared to non-inoculated control plants (Table 4). In *Jatropha*, individual inoculation of N-fixer (LI and RI) or its mixed-inoculation produced significant increases in number of leaves, chlorophyll content, seedling vigour, rate of germination and biomass compared to control plants or plants individually-inoculated with LI or RI. Under greenhouse condition, the AR activity in the control plants are much lower, a likely consequence of less cross-contamination.

TABLE 4

Seedling Vigour Index, Number of Leaves and Germination Rate of N-Fixer-Treated *Jatropha* seeds (45 DAS)

| Treatments[†] | No. of Leaves | Relative Chlorophyll | Nitrogenase activity[‡] | SVI | RG | Biomass (g) |
|---|---|---|---|---|---|---|
| Control | 6.19 ± 0.29 | 34.91 ± 3.91 | 4.15 ± 0.25 | 901.7 ± 46.7 | 23.50 ± 2.5 | 46.12 ± 6.12 |
| Root isolates (RI) | 6.58 ± 0.48 | 36.08 ± 4.08 | 8.56 ± 1.06 | 1054.1 ± 60.18 | 24.55 ± 2.55 | 62.0 ± 4.0 |

TABLE 4-continued

Seedling Vigour Index, Number of Leaves and Germination Rate of N-Fixer-Treated *Jatropha* seeds (45 DAS)

| Treatments[†] | No. of Leaves | Relative Chlorophyll | Nitrogenase activity[‡] | SVI | RG | Biomass (g) |
|---|---|---|---|---|---|---|
| Leaf isolates (LI) | 6.47 ± 0.42 | 38.81 ± 4.31 | 16.79 ± 2.79 | 986.2 ± 65.22 | 23.57 ± 2.57 | 61.4 ± 3.4 |
| RI + LI | 6.72 ± 0.42 | 35.31 ± 3.81 | 11.52 ± 1.72 | 1037.6 ± 67.51 | 25.41 ± 2.41 | 63.0 ± 4.0 |

Note:
[†]Average of 150 *Jatropha* seedlings.
[‡]Value expressed in nmol $C_2H_4$ $day^{-1}$ $seedlings^{-1}$. Each value represents the means of four replicates per treatment. Seedling vigour index (SVI) was calculated using the formula: SVI = % germination × seedling length (shoot length + root length) in cm (Baki and Anderson, 1973). Rate of germination (RG) was calculated using the following formula, RG = Σ Ni/Di where Ni is the number of germinated seeds in a given time, and Di is the time unit (day) (Madhaiyan et al., 2004).

The plant growth promoting effect can be observed in extended period in Ø35 cm pots. Significant improvements in plant height, stem diameter, leaf number and stem volume were observed (Table 5). Soil with poor nutrient content was used and a commercial NPK fertilizer was applied at half of the recommended dose (0.5 g/plant) once in 15 days intervals.

TABLE 5

Combined Inoculation of N-Fixer on the Early Growth of *Jatropha* (90 DAS)

| Treatments | Plant height (cm) | Stem Diameter | No. of leaves | Relative chlorophyll content | Stem Volume |
|---|---|---|---|---|---|
| Control | 32.23 | 25.55 | 11.58 | 26.20 | 167.41 |
| RI | 40.37 | 27.72 | 20.58 | 33.40 | 244.08 |
| RI + LI | 43.97 | 27.44 | 24.50 | 38.16 | 261.59 |

Note:
Each value is the mean of 12 plants per treatment (n = 12).
Leaf isolates (LI): L2-4 (*Methylobacterium* sp.) and L7-515 (*Methylobacterium* sp.);
Root isolates (RI): R4-368 (*Enterobacter* sp.), R5-362 (*Enterobacter* sp.), R5-431 (*Klebsiella* sp.), R7-601 (*Sinorhizobium* sp.) and R1-99 (*Rhizobium* sp.).

Example 12

Effects of *Methylobacterim* sp Inoculation in Cotton, Castor Bean, and *Sorghum*

Seeds were surface sterilized by immersion in 70% ethanol, 1 min; 2% NaOCl for 30 sec followed by 5-10 rinsing in sterile distilled water. For plant inoculation experiments, *Methylobacterium* strain L2-4 was grown in liquid 2xYT medium containing 30 mM methanol (v/v) to mid-exponential growth phase, centrifuged, washed, resuspended in sterile distilled water and stored in 4° C. until use. For seed imbibitions, the surface sterilized seeds were soaked in a double volume of bacterial culture ($OD_{600\ nm}$=1.2 or $10^9$ cfu $ml^{-1}$ of culture). After 6 h soaking, the culture was drained, and the seeds were dried in shade for 30 min before being allowed to sprout for another 24 h prior to sowing. For phyllosphere spray, the cultures were applied using a hand sprayer (approximately 25 ml per plant; $OD_{600\ nm}$=1.2) at 15 DAS.

Under greenhouse conditions, *Methylobacterium* strain L2-4 showed good AR activity in leaves of cotton, castor, sorghum, and rice (Table 6). The effects on crop growth are shown in Table 7.

TABLE 6

Nitrogenase (or Acetylene-Reduction) Activity of Various Crops Inoculated with *Methylobacterium* sp. strain L2-4 (20 DAI)

| Crops | AR-activity (nmol $C_2H_4$ $d^{-1}$ $seedlings^{-1}$) | AR-activity (nmol $C_2H_4$ $d^{-1}$ $g^{-1}$ sample (DW) |
|---|---|---|
| Cotton | 176.67 ± 21.67 | 70.7 ± 11.72 |
| *Sorghum* | 259.61 ± 59.61 | 177.8 ± 28.77 |
| Castor bean | 25.78 ± 5.78 | 19.2 ± 5.20 |
| Rice | 17.54 ± 2.54 | 140.8 ± 15.77 |
| Jatropha (MD-44) | 288.45 ± 78.45 | 114.5 ± 19.46 |

Note:
Each value is the mean ± SD of three replications per treatment.

TABLE 7

Effect of Inoculation of *Methylobacterium* sp. L2-4 on Crop Growth

| Crops | Plant height (cm) Control | Plant height (cm) Treated | No. of leaves (#) Control | No. of leaves (#) Treated | Relative chlorophyll content* Control | Relative chlorophyll content* Treated | No. of branches (#) Control | No. of branches (#) Treated | Number flower (#) Control | Number flower (#) Treated |
|---|---|---|---|---|---|---|---|---|---|---|
| Cotton | 101.5 ± 4.45 | 103.4 ± 3.08 | 40 ± 2.16 | 44.25 ± 1.89 | 35.95 ± 1.12 | 39.195 ± 1.89 | 5.75 ± 0.50 | 8.75 ± 0.96 | 9.25 ± 1.5 | 15.75 ± 1.26 |
| Castor bean | 105.8 ± 12.21 | 115.8 ± 3.92 | 10 ± 2.16 | 12.25 ± 1.50 | 49.95 ± 4.28 | 54.575 ± 1.97 | ND | ND | 0 | 2 (4) |
| *Sorghum* | 146.5 ± 31.41 | 138.3 ± 23.45 | 17 ± 2.16 | 19.25 ± 4.99 | 51.08 ± 4.04 | 61.15 ± 3.61 | ND | ND | 1.5 ± 1.0 | 1.5 ± 0.58 |
| Jatropha | 70.8 ± 1.71 | 72.0 ± 2.45 | 16.75 ± 0.5 | 20.75 ± 4.50 | 30.66 ± 0.97 | 34.18 ± 1.62 | ND | ND | ND | ND |

Note:
Each value is the mean ± SD of four replications per treatment. Relative chlorophyll content was measured 5 leaves from top of the plants. Results were recorded at 75 days after inoculation.

Example 13

AR Activity and Taxonomy Classification data of *Pleomorphomonas jatrophae*

Figure 6A:
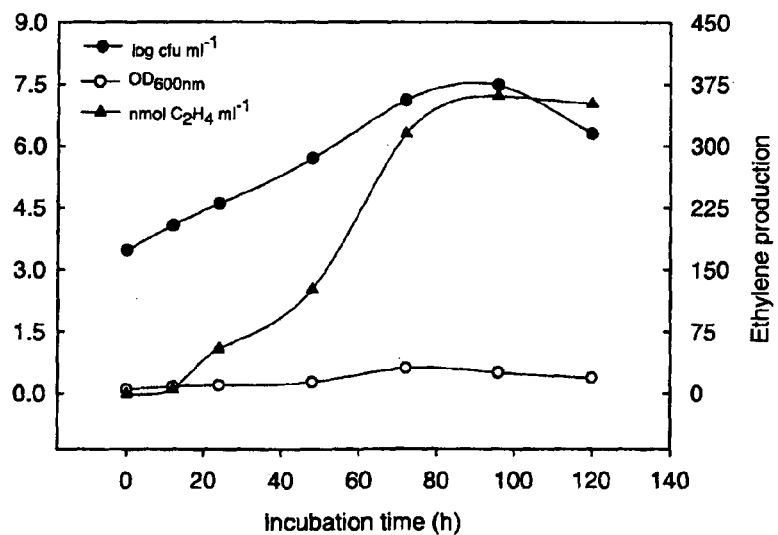
FIGS. 6a and 6b show the nitrogenase activity of *Pleomorphomonas jatrophae* strain R5-392.
Figure 6B:
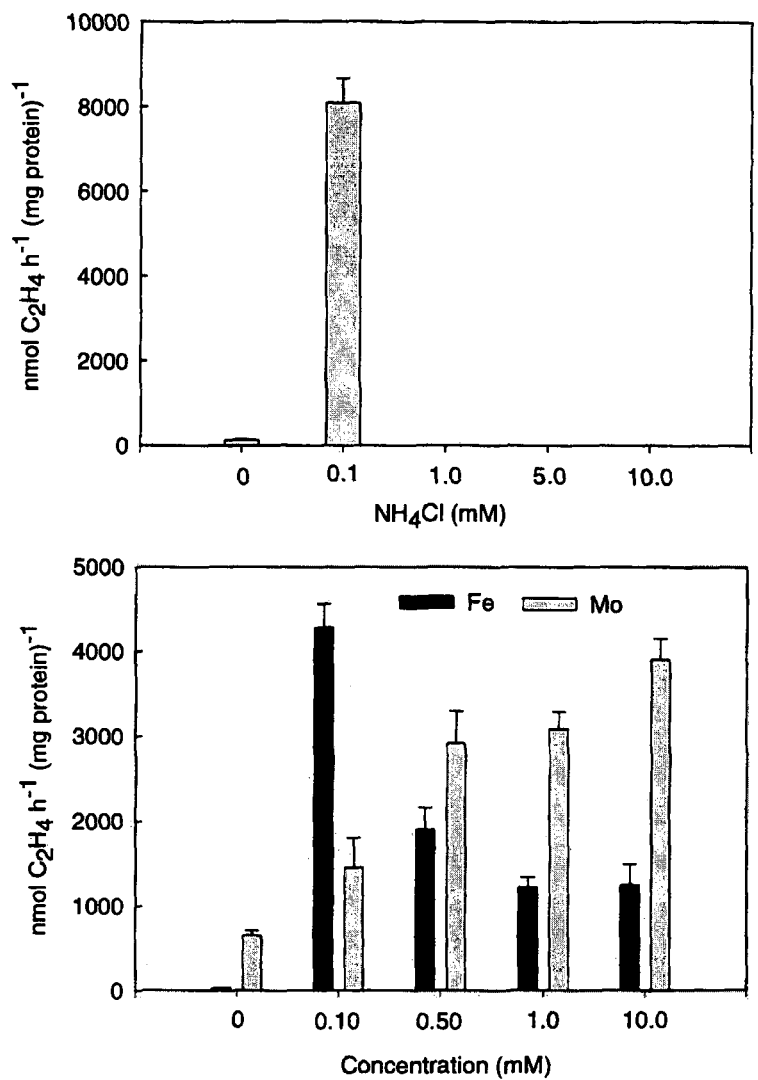

The N-fixation ability could be proved by a multidisciplinary approach. Strain R5-392$^T$ was subjected to a nifH-specific PCR amplification. The expected 409 by amplification product was observed with strain R5-392 tested. In the case of strain R5-392, this PCR product was purified and sequenced. The comparison of the resulting sequence with the EMBL database revealed a similarity with the nifH gene of *P. oryzae* of 98%. The resulting amino acid (130 deduced amino acids) sequence had 100% similarity to the ATP-dependent reductase or nitrogenase iron-protein (nitrogenase component II, dinitrogenase reductase, nifH protein) of *P. oryzae*. The nitrogenase activity of the strain R5-392 was tested by the acetylene-reduction assay method. Strain R5-392$^T$ grown in N-free medium, effectively reduced acetylene and exhibited highest nitrogenase activity of >300 nmol $C_2H_4$ ml$^{-1}$ in the headspace gas sample after 96 h incubation at 30° C. with the population increase of >6 log CFU ml$^{-1}$ (FIG. 6a). However, close relatives of R5-392 showed less than 10 nmol $C_2H_4$ produced per mg of protein (data not shown). Lower concentrations of nitrogen (0.1 mM NH4Cl) in N-free medium have triggered higher nitrogenase activity than higher concentrations or no NH$_4$Cl in the medium (FIG. 6b). Nitrogenase system was switched-off using NH4Cl at concentrations >1 mM in the N-free medium. Nitrogenase activity was measured by supplementing $Na_2MoO_4$/$FeSO_4$.$7H_2O$ at various concentrations (0, 0.1, 0.5, 1, 10 mM) in N-free medium and injected with 15% acetylene (v/v) after inoculation. Nitrogenase activity was higher in 0.1 mM Fe concentration and reduced with increasing concentrations of Fe. No nitrogenase activity was recorded in N-free medium without Fe (FIG. 6b).

Example 14

Genome Analysis for *Enterobacter* sp R4-369 and *Methylobacterium* sp. L2-4

Figure 4A:
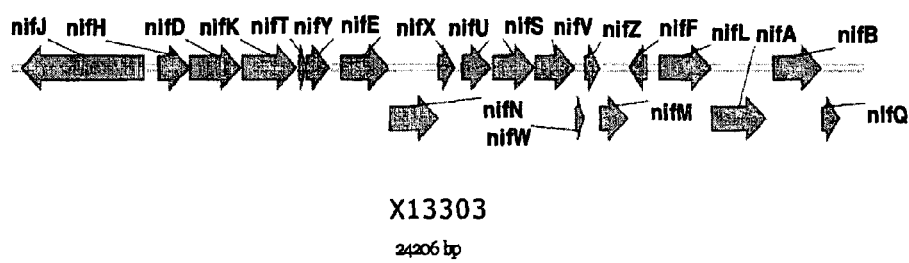
FIGS. 4a and 4b show the nitrogen-fixation gene cluster in *Klebsiella pneumonia* (Genbank No X13303) (FIG. 4a) and the homologous proteins as identified by BLASTP in *Enterobacter* sp R4-368 (SEQ ID NO:3) (FIG. 4b).
Figure 4B:
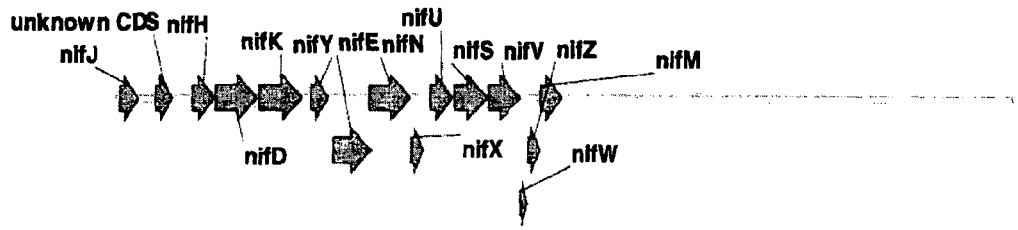

Total DNA was extracted for *Enterobacter* sp R4-369 and *Methylobacterium* sp. L2-4 and a partial genomic sequence was obtained for short-gun sequencing by the 454 pyrosequencing. Using the *Klebsiella pneumonia* nif gene cluster as a query (Genbank No 13303), a full set of nif genes were identified (FIG. 4). The sequence for *Methylobacterium* sp. L2-4 is set forth in SEQ ID NO:3. In contrast, no such genes can be identified in either *Enterobacter cloacae* (GenBank Accession Nos. NC_014121.1 and NC_014618.1) nor the endophytic plant growth-promoting *Enterobacter* sp. 638 (GenBank Accession No. NC_009436.1).

Figure 5:
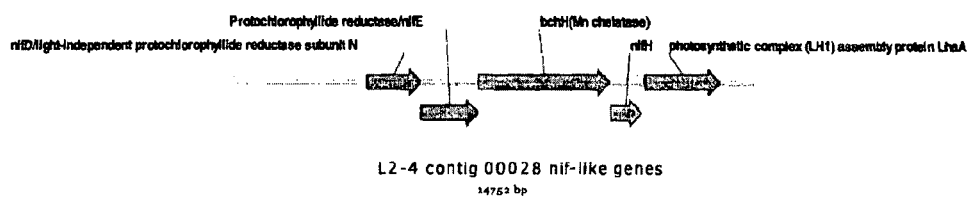
FIG. 5 shows the putative proteins encoded in SEQ ID NO:4 as identified by BLASTP.

Surprisingly, no clear homologue was found in the genome of *Methylobacterium* sp. L2-4 nor the published *Methylobacterium radiotolerans* JCM 2831 genome (GenBank Accession Nos. CP001001-CP001009), which share about 99% sequence identity in 16S rDNA and total sequence. A Blast search using the K pneumonia nifH protein sequence as query identified distantly related proteins, GenBank Accesssion Nos. YP_001755485.1 and YP_001754523.1 that share about 35% amino acid identity and was predicted to encode the chlorophyllide reductase iron protein subunit X and protochlorophyllide reductase iron-sulfur ATP-binding protein respectively. This is much lower than that between the *K. pneumonia* nifH and cyanabacteria nifH (GenBank Accession No.ACC79194.1). The genome also lack obvious nif gene cluster. SEQ ID NO:7 encode a putative nifH orthologue. Interestingly, the neighboring putative coding sequences for protochlophyllide reductase subunits share significant homology to nifD and nifE (FIG. 5). As L2-4 is able to fix nitrogen, it is probable that these genes are critical for nitrogen-fixation in *Methylobacterium*.

Example 15

Effect of EPS Production on N-Fixation in *Enterobacter*

N-fixing defective mutants were identified by Tn5 mutagenesis. EPS mutants were identified as small non-motile colonies on N-free solid medium. All EPS mutants have negligible nitrogenase activity as determined by AR assay. Some of the mutants are summarized in Table 8.

TABLE 8

EPS Mutants

| Mutant ID | Gene inserted | Tn5 flanking sequence (SEQ ID NO:) |
|---|---|---|
| S238 | Colanic acid polymerase | cgttaatctcaatttggctcagcatcaaacagtttggtat (5) |
| S236 | EPS exporter | gcgttggcccaggggatgtgctgaacgtaaccgtg (6) |
| S210 | Colanic acid acetyltransferase WcaF | ccccgcaggtgctgtatcgctggcgcgcatt (7) |
| S237 | GDP-L-fucose synthetase | ctggtgctgcgttcccgcgaggagctgaacc (8) |
| S300 | Colanic acid biosynthesis UDP-glucose lipid carrier transferase WcaJ | cgtctgaacgttgaatcgcggcacgacgagga (9) |

Example 16

Genome Sequencing and 16S rRNA Gene Amplification and Sequencing

Genomic DNA extractions were carried out according to standard protocol (Wilson, 1997) and purified using DNeasy mini spin column (Qiagen Cat. No.: 69106) and sequenced using Genome Sequencer FLX Titanium (GS-FLX Titanium) technology at Macrogen (Republic of Korea). Shot-gun sequencing and mate-pair end sequencing (3 kb) were performed and sequence assembly of quality filtered reads was performed using a GS De Novo assembler (v 2.6).

16S rRNA gene was amplified using universal primers 27F and 1492R were used (Delong, 1992). Cycling conditions were as follows: initial denaturation for 10 min at 95° C.; then 30 cycles of 1.5 min at 95° C., 1.5 min at 55° C. and 1.5 min at 72° C.; and a final extension for 10 min at 72° C. PCR products were ligated into a plasmid vector pGEM-T Easy (Promega, Madison, USA) and transformed into competent cells of *Escherichia coli* strain XL-Blue by using a pGEM-T Easy Vector System (Promega). After the transformants were cultured overnight at 37° C. on Luria-Bertani (LB) agar plates containing ampicillin (100 µg ml$^{-1}$), positive transformants were cultured overnight on LB liquid medium. Plasmids were prepared by using QIAprep Miniprep (Qiagen). Sequences of the 16S rRNA genes were obtained by using primers 27F (5'-AGAGTTTGATCMTG-GCTC-3'; SEQ ID NO:15), 1492R (5'-TACCTTGTTAC-GACTT-3'; SEQ ID NO:16), 785F (5'-GGATTAGATAC-CCTGGTA-3'; SEQ ID NO:17), 518R (5'-GTATTACCGCGGCTGCTGG-3'; SEQ ID NO:18), 1100R (5'-GGGTTCGCTCGTTG-3'; SEQ ID NO:19) and their nucleotide sequences were determined with an Applied Biosystems 3730 XI DNA sequencer (AB Applied Biosystems, HITACHI). The 16S rDNA sequences were aligned by using the Megalign program of DNASTAR. Sequence similarity analyzed by the EzTaxon server (http://www.eztaxon.org/) (Chun et al., 2007).

Example 17

Effect of Inoculation of *Enterobacter* and *Methylobacterium* Sp on Oil Palm

Seedling of micropropagated interspecies oil palm hybrid clones which were potted in non-sterilized soil were inoculated by pouring into the soil (for enterobacter R4-368) or sprayed until dripping to the leaves (for *Methylobacterium* sp L2-4). Plants were grown in the open air. Compared with mocked inoculated plants, plant height was significantly improved when inoculated both strains. For leaf number, all treatment gave a significantly higher leaf numbers (Table 8). These results were associated with a higher endophytic nitrogen fixing bacteria counts in the root and on the upper leaf surface (Table 10).

TABLE 10

Nitrogen Fixing Bacteria Counts at 150 Days After Inoculation

| Treatments | Root population[1] cfu per g | STDEV | leaf population[2] cfu/cm2 | STDEV |
|---|---|---|---|---|
| Mock inoculated | 1.27 × 10^6 | 0.20 | 0 | 0 |
| L2-4 | Nd | | 7.33 | 0.88 |
| R4-368 | 3.68 × 10^6 | 0.05 | Nd | |
| L2-4 + R4-368 | 1.85 × 10^7 | 0.22 | 8.00 | 1.73 |

Note:
[1]root were surface-sterlized before glinding.
[2]Non-sterlized upper leaf surface were imprinted on agar plates and the red-pigmented colonies were scored 3 days after incubation in 30° C.

Example 18

Effect of Nitrogen-Fixation Genes on Growth Promotion and Leaf N Content

Knockout mutant of nifH, nifD and nifK genes were created in *Enterobacter* R4-368 by electroporation of the respective knockout construct containing about 1 kb flanking sequences fused at both sides of a synthetic mini-Tn5 transposon (Kanamycin resistant). Clean knockout mutants were confirmed by PCR and Southern blotting. The mutant and wildtype strains were inoculated to the root system of plants derived from surface sterilized Jatropha curcas seeds and potted in sterilized sand and vermiculite (1:1) mix. Inoculation was done by pouring 100 ml cell preparation (1 OD600 in water) into each pot. Plants were grown in open air in a greenhouse. Plant height, number of leaves and dry biomass were measured at 45 days after inoculation. Dried leaf biomass (~2 mg) from 4 plants was also subjected to nitrogen content analysis, which was done with the Elementar Vario Micro Cube (ELEMENTAR Analysensysteme, Germany). As can be seen in Table 11, all knockout mutants showed similar plant height, leaf number, biomass and N content to mock inoculated plants whereas significant improvements were observed in plants inoculated with wildtype *Enterobacter* sp. R4-368.

TABLE 9

Plant Height and Leave Number at 150 Days After Inoculation

| Plant series No. | P1 | P2 | P3 | P4 | P5 | P6 | P7 | P8 | P9 | Avr | STDEV | P value |
|---|---|---|---|---|---|---|---|---|---|---|---|---|
| Plant Height | | | | | | | | | | | | |
| Mock inoculated | 60 | 55 | 56 | 35 | 61 | 54 | 59 | 60 | 55 | 55.00 | 7.94 | |
| L2-4 | 42 | 55 | 52 | 69 | 53 | 68 | 57 | 67 | 51 | 57.11 | 9.16 | |
| R4-368 | 57 | 54 | 58 | 65 | 61 | 61 | 60 | 69 | 59 | 60.44 | 4.42 | 0.09 |
| L2-4 + R4-368 | 56 | 63 | 66 | 68 | 48 | 61 | 69 | 65 | 71 | 63.00 | 7.21 | 0.04 |
| Leave Number | | | | | | | | | | | | |
| Mock inoculated | 10 | 10 | 9 | 11 | 10 | 10 | 11 | 10 | 10 | 10.11 | 0.60 | |
| L2-4 | 12 | 13 | 13 | 13 | 13 | 12 | 12 | 13 | 13 | 12.67 | 0.50 | 0.0005 |
| R4-368 | 11 | 11 | 12 | 12 | 12 | 12 | 12 | 11 | 11 | 11.56 | 0.53 | 0.0005 |
| L2-4 + R4-368 | 13 | 13 | 11 | 12 | 12 | 12 | 12 | 11 | 11 | 11.89 | 0.78 | 0.0005 |

TABLE 11

Effect of nifHDK Gene Deletion in *Enterobacter* sp. R4-368 at 45 Days After Inoculation

| strains | Plant height (cm)* | No. of leaves* | Shoot biomass (g)* | Root Biomass (g)* | Leaf N content (%)# |
|---|---|---|---|---|---|
| Wildtype | 34.0 ± 5.8 | 10.0 ± 2.4 | 7.1 ± 0.7 | 1.4 ± 0.1 | 1.968 ± 0.323 |
| nifHΔ | 25.3 ± 4.5 | 8.1 ± 1.2 | 4.1 ± 1.3 | 0.7 ± 0.1 | 1.055 ± 0.013 |
| nifDΔ | 23.1 ± 4.5 | 7.1 ± 1.2 | 4.4 ± 0.4 | 0.6 ± 0.1 | 0.878 ± 0.019 |
| nifKΔ | 22.6 ± 3.9 | 7.3 ± 1.3 | 4.4 ± 0.5 | 0.8 ± 0.1 | 1.263 ± 0.025 |
| mock | 17.9 ± 1.3 | 6.1 ± 1.2 | 2.6 ± 0.5 | 0.6 ± 0.0 | 0.903 ± 0.025 |

*n = 7;
n = 4

Example 19

Effect of EPS Gene Cluster on Plant Colonization

*Jatropha* seed (cultivar MD-44) coats were removed, seed kernel were sterilized with 75% ethanol (v/v) for 1 min followed by 10% H2O2 (v/v) for 60 min followed by five subsequent rinses in sterile distilled water (SDW) and immersed in SDW overnight at 28° C. in darkness. The endosperm-free embryos were germinated on hormone-free seed germination medium (½ MS salt, B5 Vitamins, 5 g/L sucrose, 0.5 g/L MES and 2.2 g/L phytagel, pH 5.6) and cultured in a tissue culture room, at 25° C.±2° C. in a 16 h light (100 μmol/m28)/8 h dark cycle. Strains used are wild-type *Enterobacter* sp. R4-368 , Tn5 mutant S300 which contains a Tn5 transposon in the EPS gene cluster and produce very little EPS and the knockout mutant that has the whole EPS gene cluster deleted. The mutant and wildtype strains were inoculated to the root system of plants derived from surface sterilized Jatropha curcas seeds and potted in sterilized sand and vermiculite (1:1) mix. Inoculation was done by pouring 100 ml cell preparation (1 OD600 in water) into each pot. Plants were grown in open air in a greenhouse with regular watering of water or nutrient solutions. Both the Tn5 mutant and knockout mutant of the EPS genes showed significant reduction (p<0.05) in plant heights and biomass (Table 12).

TABLE 12

Effect of *Enterobacter* or EPS Genes on *Jatropha* Growth Promotion

| Strains | Plant height (cm)[1] | Dry biomass (g)[2] | |
|---|---|---|---|
| | | Shoot | Root |
| *Enterobacter* sp. R4-368 | 28.1 ± 2.90 | 9.50 ± 0.57 | 1.74 ± 0.04 |
| Knockout EPS 130-1 | 24.9 ± 2.90 | 6.75 ± 0.76 | 1.15 ± 0.17 |
| sTn5 mutant S300 | 26.0 ± 1.50 | 6.90 ± 0.31 | 1.14 ± 0.12 |
| Mock innoculated | 23.3 ± 2.30 | 7.57 ± 0.30 | 0.96 ± 0.20 |

Note:
Each value represents the mean and SD of 7 plants.
[1]30 days after inoculation.
[2]45 days after inoculation.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. For example, if the range 10-15 is disclosed, then 11, 12, 13, and 14 are also disclosed. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the pracfice of the invention.

It will be appreciated that the methods and compositions of the instant invention can be incorporated in the form of a variety of embodiments, only a few of which are disclosed herein. Embodiments of this invention are described herein, including the best mode known to the inventors for carrying out the invention. Variations of those embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

BIBLIOGRAPHY

Antoun H, Beauchamp C J, Goussard N, Chabot R, Lalande R: Potential of *Rhizobium* and *Bradyrhizobium* species as plant growth promoting rhizobacteria on non-legumes: Effect on radishes (*Raphanus sativus* L.). *Plant and Soil* 1998, 204(1):57-67.

Baldani J I, Reis V M, Baldani V L D, Döbereiner J: Review: A brief story of nitrogen fixation in sugarcane-reasons for success in Brazil. *Functional Plant Biology* 2002, 29(4):417-423.

Baldani V L D, Döbereiner J: Host-plant specificity in the infection of cereals with *Azospirillum* spp. *Soil biology and biochemistry* 1980, 12(4):433-439.

Barac T, Taghavi S, Borremans B, Provoost A, Oeyen L, Colpaert J V, Vangronsveld J, Van Der Lelie D: Engineered endophytic bacteria improve phytoremediation of water-soluble, volatile, organic pollutants. *Nature biotechnology* 2004, 22(5):583-588.

Barton P K, Atwater J W: Nitrous Oxide Emissions and the Anthropogenic Nitrogen in Wastewater and Solid Waste, vol. 128: ASCE; 2002.

Boddey R, Oliveira O C, Urquiaga S, Reis V, Olivares F L, Baldani V, Döbereiner J: Biological nitrogen fixation associated with sugar cane and rice: contributions and prospects for improvement. *Plant and Soil* 1995, 174(1):195-209.

Borthakur D, Barber C, Lamb J, Daniels M, Downie J, Johnston A: A mutation that blocks exopolysaccharide synthesis prevents nodulation of peas by Rhizobium leguminosarum but not of beans by R. phaseoli and is corrected by cloned DNA from. Rhizobium or the phytopathogen Xanthomonas. *Molecular and General Genetics MGG* 1986, 203(2):320-323.

Chaintreuil C, Giraud E, Prin Y, Lorquin J, Ba A, Gillis M, De Lajudie P, Dreyfus B: Photosynthetic bradyrhizobia are natural endophytes of the African wild rice *Oryza brevilligulata*. *Applied and environmental microbiology* 2000, 66(12):5437.

Chang M C Y: Harnessing energy from plant biomass. *Curr Opin Chem Biol* 2007, 11(6):677-684.

Chun, J. S., Lee, J. H., Jung, Y. Y., Kim, M. J., Kim, S., Kim, B. K., Lim, Y. W. (2007) EzTaxon: a web-based tool for the identification of prokaryotes based on 16S ribosomal RNA gene sequences. Int. J. Syst. Bacteriol. 57, 2259-2261.

Crutzen P J, Mosier A R, Smith K A, Winiwarter W: N2O release from agro-biofuel production negates global warming reduction by replacing fossil fuels. *Atmospheric Chemistry and Physics* 2008, 8(2):389-395.

Delong, E. F. (1992) Archaea in coastal marine environments. Proc. Natl. Acad. Sci. USA 89, 5685-5689.

Dreyfus B, Dommergues Y: Nitrogen-fixing nodules induced by Rhizobium on the stem of the tropical legume Sesbania rostrata. *FEMS Microbiology Letters* 1981, 10(4):313-317.

Eaglesham A, Szalay A: Aerial stem nodules on *Aeschynomene* spp. *Plant Science Letters* 1983, 29(2-3):265-272.

Elbeltagy A, Nishioka K, Sato T, Suzuki. H, Ye B, Hamada T, Isawa T, Mitsui H, Minarnisawa K: Endophytic colonization and in planta nitrogen fixation by a Herbaspirflum sp. isolated from wild rice species. *Applied and environmental microbiology* 2001, 67(11):5285-5293.

Fairless D: Biofuel: The little shrub that could—maybe. *Nature* 2007, 449:652-655.

Galloway J N, Townsend A R, Erisman J W, Bekunda M, Cai Z, Freney J R, Martinelli L A, Seitzinger S P, Sutton M A: Transformation of the nitrogen cycle: recent trends, questions, and potential solutions. *Science* 2008, 320(5878):889-892.

Gaydou A M, Menet L, Ravelojaona G, Geneste P: Vegetable energy sources in Madagascar: ethyl alcohol and oil seeds. *Oleagineux* 1982, 37((3)):135-141.

Gottfert M, Rothlisberger S, Kundig C, Beck C, Marty R, Hennecke H: Potential symbiosis-specific genes uncovered by sequencing a 410-kilobase DNA region of the *Bradyrhizobium japonicum* chromosome. *Journal of bacteriology* 2001, 183(4):1405.

Jourand P, Giraud E, Bena G, Sy A, Willems A, Gillis M, Dreyfus B, de Lajudie P: *Methylobacterium nodulans* sp. nov., for a group of aerobic, facultatively methylotrophic, legume root-nodule-forming and nitrogen-fixing bacteria. *International journal of systematic and evolutionary microbiology* 2004, 54(6):2269-2273.

Jourand P, Renier A, Rapior S, de Faria S M, Prin Y, Galiana A, Giraud E, Dreyfus B: Role of methylotrophy during symbiosis between Methylobacterium nodulans and Crotalaria podocarpa. *Molecular plant-microbe interactions* 2005, 18(10):1061-1068.

Kaneko T, Nakamura Y, Sato S, Asamizu E, Kato T, Sasamoto S, Watanabe A, Idesawa K, Ishikawa A, Kawashima K: Complete genome structure of the nitrogen-fixing symbiotic bacterium Mesorhizobium loti. *DNA research* 2000, 7(6):331-338.

Kennedy I R, Pereg-Gerk L L, Wood C, Deaker R, Gilchrist K, Katupitiya S: Biological nitrogen fixation in non-leguminous field crops: Facilitating the evolution of an effective association between Azospirillum and wheat. *Plant and Soil* 1997, 194(1):65-79.

Liu Y, Wang H, Sun X, Yang H, Wang Y, Song W: Study on mechanisms of colonization of nitrogen-fixing PGPB, *Klebsiella pneumoniae* NG14 on the root surface of rice and the formation of biofilm. *Curr Microbiol* 2011, 62(4):1113-1122.

Long S R: Rhizobium symbiosis: nod factors in perspective. *The Plant Cell* 1996, 8(10):1885.

Madhaiyan M, Poonguzhali S, Senthilkumar M, Seshadri S, Chung H Y, Yang J C, Sundaram S P, Sa T M: Growth promotion and induction of systemic resistance in rice cultivar Co-47 (*Oryza sativa* L.) by *Methylobacterium* spp. *Bot Bull Acad Sin* 2004, 45:315-324.

Maxwell C A, Hartwig U A, Joseph C M, Phillips D A: A chalcone and two related flavonoids released from alfalfa roots induce nod genes of *Rhizobium meliloti*. *Plant physiology* 1989, 91(3):842.

Melillo J M, Reilly J M, Kicklighter D W, Gurgel A C, Cronin T W, Paltsev S, Felzer B S, Wang X, Sokolov A P, Schlosser C A: Indirect Emissions from Biofuels: How Important? *Science* 2009, 326(5958):1397-1399.

Moir J W B: Nitrogen cycling in bacteria: molecular analysis: Caister Academic Press; 2011.

Openshaw K: A review of *Jatropha curcas:* an oil plant of unfulfilled promise. *Biomass Bioenergy* 2000, 19(1):1-15.

Pedraza R O: Recent advances in nitrogen-fixing acetic acid bacteria. *Int J Food Microbiol* 2008, 125(1):25-35.

Peters N K, Frost J W, Long S R: A plant flavone, luteolin, induces expression of Rhizobium meliloti nodulation genes. *Science* 1986, 233(4767):977.

Pinto-Tomás A A, Anderson M A, Suen G, Stevenson D M, Chu F S T, Cleland W W, Weimer P J, Currie C R: Symbiotic Nitrogen Fixation in the Fungus Gardens of Leaf-Cutter Ants. *Science* 2009 326(5956):1120-1123.

Rediers H, Vanderleyden J, De Mot R: Azotobacter vinelandii: a *Pseudomonas* in disguise? *Microbiology* 2004, 150(5):1117-1119.

Renier A, De Faria. S M, Jourand P, Giraud E, Dreyfus B, Rapior S, Prin Y: Nodulation of Crotalaria podocarpa DC. by Methylobacterium nodulans displays very unusual features. *Journal of Experimental Botany* 2011, 62(10):3693-3697.

Saravanan V S, Madhaiyan M, Osborne J, Thangaraju M, Sa T M: Ecological occurrence of Gluconacetobacter diazotrophicus and nitrogen-fixing Acetobacteraceae members: their possible role in plant growth promotion. *Microb Ecol* 2008, 55(1):130-140.

Senthilkumar M, Madhaiyan M, Sundaram S, Kannaiyan S: Intercellular colonization and growth promoting effects of *Methylobacterium* sp. with plant-growth regulators on rice (*Oryza sativa* L. Cv CO-43). *Microbiological research* 2009, 164(1):92-104.

Stacey G, So J S, Lakshmi S K B, Carlson R W: A lipopolysaccharide mutant of Bradyrhizobium japonicum that uncouples plant from bacterial differentiation. *Molecular plant-microbe interactions* 1991, 4(4):332-340.

Wilson, K. (1997). Preparation of genomic DNA from bacteria, p. 2.4.1-2.4.5. In F. M. Ausubel, R. Brent, R. E. Kingston, D. D. Moore, J. G. Seidman, J. A. Smith and K. Struhl (ed.), Current Protocols in Molecular Biology. J. Wiley & Sons, New York, N.Y.

Whittenbury R, Phillips K, Wilkinson J: Enrichment, isolation and some properties of methane-utilizing bacteria. *Journal of General Microbiology* 1970, 61(2):205.

Widmer F, Shaffer B T, Porteous L A, Seidler R J: Analysis of nifH gene pool complexity in soil and litter at a Douglas fir forest site in the Oregon cascade mountain range. *Appl Environ Microbiol* 1999, 65(2):374-380.

Young J, Johnston A: The evolution of specificity hi the legume-Rhizobium symbiosis. *Trends in Ecology & Evolution* 1989, 4(11):341-349.

Zehr J P: Nitrogen fixation by marine cyanobacteria. *Trends in microbiology* 2011, 19(4):162-173.

What is claimed is:

1. A bacterial inoculant for application to plants, said bacterial inoculant comprising an effective quantity of a biologically pure culture of at least one bacterial species, trace metal ions and a carrier;
    wherein the trace metal ions are selected from the group consisting of molybdenum ($Mo^{2+}$) ions, iron ($Fe^{2+}$) ions, manganese ($Mn^{2+}$) ions, and any combination of these ions;
    wherein the carrier is selected from the group consisting of a biopolymer, a sugar, an animal milk, a planting material and a porous, chemically inert carrier;
    wherein the at least one bacterial species is *Enterobacter* species R4-368 (NRRL B-50631); and
    wherein the bacterial species reduces acetylene to ethylene or reduces atmospheric nitrogen ($N_2$) to ammonia ($NH_3$) and improves plant productivity when the bacterial inoculant is applied to a plant.

2. The bacterial inoculant of claim 1, wherein the reduction occurs on the leaf surface, inside the leaf surface, inside the root tissue or on the surface of the root system.

3. The bacterial inoculant of claim 1, wherein the reduction occurs in association with a plant selected from the group of plant species of a *Jatropha* genus, *Sorghum* genus, *Gossypium* genus, *Elaeis* genus, *Ricinus* genus, *Oryza* genus and *Manihot* genus.

4. The bacterial inoculant of claim 1, further comprising a bacterial species selected from the group consisting of *Pleomorphomonas jatrophae* R5-392 (NRRL B-50630), *Methylobacterium* sp. L2-4 (NRRL B-50628), *Methylobacterium* sp. L2-76 (NRRL B-50629), *Sphingomonas* sp. S6-274 (NRRL B-50632) and any combination thereof.

5. The bacterial inoculant of claim 1, wherein the bacterial species secrets exopolysaccharide (EPS) or endoglucanase.

6. The bacterial inoculant of claim 1, wherein the concentration of the trace metal ions in the inoculant is between about 0.1 mM and about 50 mM.

7. A method of improving plant productivity comprising inoculating a plant with an effective quantity of the bacterial inoculant of claim 1.

8. The method of claim 7, wherein the bacterial inoculant is sprayed on aerial plant parts.

9. The method of claim 7, wherein the bacterial inoculant is applied by inserting into a planting furrow, watering the plant root system in the soil, dipping the roots in the bacteria inoculant or coating seeds.

10. The method of claim 7, wherein the concentration of the trace metal ions in the inoculant is between about 0.1 mM and about 50 mM.

11. The method of claim 10, wherein the bacterial inoculant is sprayed on aerial plant parts.

12. The method of claim 7, wherein the plant productivity is plant growth, maintenance of high chlorophyll content in leaves, increasing fruit or seed numbers, increasing fruit or seed unit weight or any combination of these characteristics.

13. The method of claim 7, wherein the plant is a species of a *Jatropha* genus, *Sorghum* genus, *Gossypium* genus, *Elaeis* genus, *Ricinus* genus, *Oryza* genus or *Manihot* genus.

14. The method of claim 10, wherein the plant productivity is plant growth, maintenance of high chlorophyll content in leaves, increasing fruit or seed numbers, increasing fruit or seed unit weight or any combination of these characteristics.

15. The method of claim 10, wherein the plant is a species of a *Jatropha* genus, *Sorghum* genus, *Gossypium* genus, *Elaeis* genus, *Ricinus* genus, *Oryza* genus or *Manihot* genus.

16. A method of improving plant productivity comprising inoculating a plant with an effective quantity of the bacterial inoculant of claim 4.

17. The method of claim 16, wherein the plant productivity is plant growth, maintenance of high chlorophyll content in leaves, increasing fruit or seed numbers, increasing fruit or seed unit weight or any combination of these characteristics.

18. The method of claim 16, wherein the plant is a species of a *Jatropha* genus, *Sorghum* genus, *Gossypium* genus, *Elaeis* genus, *Ricinus* genus, *Oryza* genus or *Manihot* genus.

19. The bacterial inoculant of claim 4, wherein the concentration of the trace metal ions in the inoculant is between about 0.1 mM and about 50 mM.

20. The method of claim 16, wherein the bacterial inoculant is sprayed on aerial plant parts.

21. The method of claim 16, wherein the bacterial inoculant is applied by inserting into a planting furrow, watering the plant root system in the soil, dipping the roots in the bacteria inoculant or coating seeds.

22. The method of claim 16, wherein the concentration of the trace metal ions in the inoculant is between about 0.1 mM and about 50 mM.

23. The method of claim 22, wherein the bacterial inoculant is sprayed on aerial plant parts.

24. The method of claim 22, wherein the plant productivity is plant growth, maintenance of high chlorophyll content in leaves, increasing fruit or seed numbers, increasing fruit or seed unit weight or any combination of these characteristics.

25. The method of claim 22, wherein the plant is a species of a *Jatropha* genus, *Sorghum* genus, *Gossypium* genus, *Elaeis* genus, *Ricinus* genus, *Oryza* genus or *Manihot* genus.

26. The method of claim 22, wherein the bacterial inoculant is applied by inserting into a planting furrow, watering the plant root system in the soil, dipping the roots in the bacteria inoculant or coating seeds.

* * * * *

SEQUENCE LISTING

```
<160> NUMBER OF SEQ ID NOS: 19

<210> SEQ ID NO 1
<211> LENGTH: 26
<212> TYPE: DNA
<213> ORGANISM: Artificial Sequence
<220> FEATURE:
<223> OTHER INFORMATION: PCR oligonucleotide primer

<400> SEQUENCE: 1
aaaggyggwa tcggyaartc caccac                                          26

<210> SEQ ID NO 2
<211> LENGTH: 26
<212> TYPE: DNA
<213> ORGANISM: Artificial Sequence
<220> FEATURE:
<223> OTHER INFORMATION: PCR oligonucleotide primer

<400> SEQUENCE: 2
ttgttsgcsg crtacatsgc catcat                                          26

<210> SEQ ID NO 3
<211> LENGTH: 13163
<212> TYPE: DNA
<213> ORGANISM: Enterobacter sp R4-368

<400> SEQUENCE: 3
atgaccatgc gtcaatgcgc catttacggc aaaggtggga tcggcaaatc gaccaccaca      60
cagaacctgg tcgccgcgct ggcggagatg ggtaaaaaag taatgattgt cggctgcgat     120
ccgaaagccg actccacgcg tttgatcctg catgcgaaag cgcagaacac cattatggag     180
atggctgctg aagttggctc cgtggaagac ctggaattag aagacgtgct gcaaatcggt     240
tacggcggcg tgcgctgcgc agaatccggc ggtccggagc caggcgtggg ttgtgccggt     300
cgtggggtga tcaccgcgat taacttcctc gaagaagaag gcgcttacgt gccggatctc     360
gattttgttt tctacgacgt gctgggcgat gtggtatgcg gtggtttcgc catgccgatt     420
cgtgaaaaca aagcgcagga gatctacatc gtttgctctg gcgaaatgat ggcgatgtac     480
gctgccaata acatctccaa aggcatcgtg aagtatgcca aatccggcaa agtgcgcctc     540
ggcgggctga tttgtaactc gcgccagacc gaccgtgaag atgagctcat cattgcgctg     600
gcagaaaaac tcggcacgca aatgatccac tttgttcccc gcgacaacat tgtgcagcgt     660
gcggaaatcc gccgtatgac ggttatcgaa tatgacccga cctgcaatca ggcaaatgaa     720
tatcgcagcc ttgccagcaa aatcgtcaac aacaccaaaa tggtggtgcc cacccctgc     780 accatggatg agctggaagc gctgctgatg gagttcggca ttatggatgt ggaagacacc     840
agcatcattg gtaaaaccgc cgccgaagaa acgccgtct gatcacagga gcacacccat     900
gagcaatgca acaggcgaac gtaacctgga gataatcgag caggtgctgg aggttttccc     960
ggagaagacg cgcaaagaac gcagaaaaca catgatggtg acggacccgg agcaggaaag    1020
```

```
cgtcggtaag tgcatcatct ctaaccgcaa atcgcagccg ggcgtgatga ccgtgcgcgg    1080
ctgctcgtat gccggatcga aagggtggta atttgggcca atcaaggata tggcgcatat    1140
ctcccacggt ccgatcggct gcgggcagta ctcccgcgcc gggcgacgta actactacac    1200
cggcgtcagc ggcgtggaca gcttcggcac gctcaacttc acctccgatt tcaggagcg    1260
tgacatcgtg tttggcggcg acaaaaagct cgccaaactg attgaagagc tggaagtgct    1320
attcccgctg accaaaggca tttcgattca gtcggaatgc ccgtcggcc tgattggcga    1380
tgacattgag gccgtcgcga acgccagtcg taaagccatc aacaaaccgg ttattccggt    1440
gcggtgcgaa ggctttcgcg gcgtgtcgca atccctcggt caccatattg ctaacgatgt    1500
gatccgcgac tgggtgctgg agaaccgcga aggcaaaccg ttcgaatcca ccccttacga    1560
tgtggcgatc atcggcgatt acaacatcgg cggcgatgcc tgggcttcgc gcattttgct    1620
cgaagagatg ggcttgcggg tggtggcgca atggtccggc gacggtacgc tggtggagat    1680
ggagaacacg ccgttcgtca aactcaacct ggtgcactgc taccgctcaa tgaactacat    1740
ctcgcgccat atggaggaga agcacggtat tccgtggatg gaatacaact tctttggccc    1800
gacgaaaatt gcggaatcgc tgcgcaaaat cgccgaccag tttgacgaca ccattcgcgc    1860
caacgccgaa gcggtgatcg cccgatacca ggcgcagaac gacgccatta tcgccaaata    1920
tcgcccacgt ctggagggtc gcaaggtgct gctttatatg ggcgggttgc gtccgcgcca    1980
tgtgattggc gcctatgaag acctgggaat ggagatcatc gcagccggtt atgagttcgc    2040
tcataacgat gattacgacc gcaccctgcc ggatctgaaa gagggcacgc tgctgtttga    2100
tgatgccagc agctatgagc tggaggcatt cgtcaacgcg ctgaaaccgg atctcatcgg    2160
ttccggcatc aaagagaagt acatctttca gaaaatgggc gtgccgtttc gccagatgca    2220
ctcctgggat tactccggcc cgtaccacgg ctatgacggc ttcgccatct tcgcccgcga    2280
tatggatatg acgctcaaca ccccgcgtg gggccagttg accgcgccgt ggctgaaatc    2340
cgcctgattt ttatcctgtt atcccgtttg ttcaccgatt tgtggcgcgg gaggagaaca    2400
ccatgagcca gactgctgag aaaatacaga attgccatcc cctgtttgaa caggatgctt    2460
accagacgct gtttgccggt aaacgggcac tcgaagaggc gcactcgccg gagcgggtgc    2520
aggaagtttt tcaatggacc accaccccgg aatacgaagc gctgaacttc aaacgcgaag    2580
cgctgactat cgacccggca aaagcctgcc agccgctggg cgcggtgctc tgttcgctgg    2640
ggtttgccaa caccctgcca tatgtgcacg gttcacaagg ttgcgtggcc tatttccgta    2700
catactttaa ccgccacttc aaagaaccgg tggcctgcgt gtcggattca atgacggaag    2760
atgcggccgt gttcggcggg aataacaacc tcaataccgg gctacaaaac gccagcgcgc    2820
tgtataaacc ggagattatc gccgtctcta ccacctgtat ggcggaggta atcggcgatg    2880
acttgcaggc ttttatcgcc aacgctaaaa aagatggttt tcttgatgcc gccatccccg    2940
tgccctacgc gcacaccccc agtttttatcg gcagccatat caccggctgg acaacatgt    3000
ttgaaggttt tgcccgtacc tttacggcag accatcaggc acagcccggt aaactttcac    3060
gcatcaacct ggtgaccggg tttgaaacct atctcggcaa ttttcgcgtg ctgaaacgca    3120
tgatggaaca aatggaggtg caggcgagtg tgctctccga tccatcagaa gtgctggata    3180
ccctgctaa cggcattac cagatgtacg cgggcgggac gacgcagcaa gagatgcgcg    3240
aggcgccgga cgctatcgac acactgctgc tgcaacccctg caactggtg aaaagcaaaa    3300
aagtggtaca ggagatgtgg aatcagcccg ccaccgaggt ttctgttccc gttgggctgg    3360
```

```
caggaacgga tgaactattg atggcgatca gtcagttaac cggcaaggcc attcccgact   3420
cgctggcgct ggagcgcggg cggctggtcg atatgatgct cgactcccac acctggctgc   3480
acggtaaaaa attcggtctg tttggcgacc cggatttttgt catgggattg acccgtttcc  3540
tgctggagct gggctgcgaa ccgaccgtta tcctctgcca taacggtaac aagcgctggc   3600
agaaagcgat gaagaaaatg ctcgacgcct caccgtacgg ccaggagagc gaagtattta   3660
tcaactgcga tttgtggcat ttccgctcgc tgatgtttac ccgccagccg gactttatga   3720
ttggcaactc gtacggcaag tttattcagc gcgacacctt agccaagggt gaacagtttg   3780
aagttccgct gatccgcctc ggttttcccc tgttcgaccg ccaccatctg caccgccaga   3840
ccacctgggg ttatgagggc gccatgagca ttctcactac ccttgtgaat gcggtactgg   3900
agaaagtaga caaagagacc atcaagctcg caaaaccga ctacagcttc gatcttatcc    3960
gttaaccatc acacgccccg cgccacgcgg ggccaggag gctctatgcc ggtcattatt    4020
cttcgccagc gcggcgcgga tctctattgc tatatcgcga acaggatct ggaagcccgc    4080
gtgttacagg ttgaacacga cacgccggaa cactgggcg gcgcgcttga acttgaaggt    4140
ggacgccgtt attacgtcaa tctgcaaccc ggccgcccgg cttttccgct cagcctgcgc   4200
gccacccgcg acgcgcaggc ataaggaggt gagcaatgtc cgacaacgat acgctgttct   4260
ggcggatgct ggcgctgttt cagtgcctgc cggagctgca acccgcgcaa atcatggcct   4320
ggctcaccca cagttgtgag gacgtgctga cacccgacgg gctggcagca ctcgaattac   4380
cgcaactgga agcccggttt ccgtatgcgg aagccctgat gtccagtggc cgctgggcgc   4440
gggttaaagc ctgcctgcgc ggcgaactgc ctgcccattt gcaggtgcag gaaacccaaa   4500
gccgccgtcc acaattggtt gtcgccttct gctcacagga tgggctcacc atcaatggtc   4560
atttcggcca ggggcgactt ttctttattt acgggtttga tgaccagggc ggctggctcc   4620
atgatttgcg ccgctaccct tctcacccgc aaaaccagga accgaatgaa atccgcgcgc   4680
agttactcca cgactgccat ttgctgtttt gtgaagcgat cggcggcccg gcagccgcac   4740
ggctaattcg tcataatatt cacccgatga agtgtcacc gggcaatacc attttgtccc    4800
agtgcgccgc catccagaac ctgctggccg ggccgttacc gccgtggctg gcgaaacggc   4860
tggaacgcgc taatccgctg gaagcgcggg tgttttaaac cgcccctga tggggcgtt     4920
ttttggcgtg ggcattgcgc caattgtctg ttttgtcaca aagcgcacaa cacttttccc   4980
ttaaaaatca atcactattt tctggcttgc gatttgcacc attaacacta acccaaccag   5040
aaaatgaggt gatgatgaag gggaacgaca tcctggccct gctcgatgaa ccggcctgtg   5100
agcataacca taaacagaaa tccggctgta gcgcgccaaa acccggtgcg actgccggag   5160
gctgcgcctt cgacggcgca cagatcaccc tgctgccact ttccgatgtg gcgcatctgg   5220
tacatggccc gattggctgc gccggtagct catgggataa ccgcggcagc ctgagttccg   5280
gcccacggat caaccggctc ggattccacca ccgatttgaa cgagcaggat gtcatcatgg   5340
ggcgtggcga gcgtcggctg tttcacgcgg tgcgccacat tgtcgaccgc tatcatccgg   5400
cggcggtatt tatttacaac acctgcgttc cggcaatgga aggcgatgat attgaagccg   5460
tctgccaggc cgcagcgacc gccaccggtg tgccgtgat tgccgttgat gtggccggtt    5520
tttacggtag caaaaacctg ggaaccgcc tggcgggcga ggtgatggtg aaaaagtca    5580
ttggcgggcg cgaacccgcg ccgtggccgg acaatacgcc ttttgccccg gcgcaccgtc   5640
atgacattgg cctgattggc gaatttaata tcgccggcga ttctggcat atccagccgc    5700
tgcttgatga gctgggcatt cgcgtcctcg gctccctgtc cggcgacggg cgctttgccg   5760
```

```
agatccagac gctgcaccgc gcgcaggtca atatgctggt ttgctccaga gcgctgatta    5820
atgtcgccag atcgctggag cagcgttacg gcacgccgtg gtttgaaggc agttttatg     5880 gcgttcgcgc cacttctgat gccctgcgcc agctggcaac gctcaccggc gatagcgatt    5940
taatggcgcg caccgaacag ctaatcacgc gtgaagaaca cgcagcagag caggcgctgg    6000
caccgctgcg cgaacgttta cgcggcagga aagtgttgct ctataccggt ggcgttaaat    6060
cctggtcggt agtttcggca ctgcaggatc tcggcatgac ggttgtggct accggaacgc    6120
gcaaatccac cgaagaggat aaacagcgca tccgtgaact gatgggcgat gacgccatca    6180
tgctggatga aggcaatgcc cgcgccctgc tggatgtggt ttatcgctgc aaagccgaca    6240
tgatgatcgc aggcggtcgc aacatgtaca ccgcttataa agcgcgtctg ccctttcttg    6300
atatcaacca ggagcgtgaa cacgcgtttg ccggttatcg cggcatcatt acccttgccg    6360
aacaactttg tcagaccctg aaagcccgg tctggccgca aacgcatgcc cgcgcgccgt     6420
ggcaataagg agcgttcaat ggccgaaatt cttcgcagta aaaaccgct ggcggtcagc     6480 ccgataaaaa gcggccagcc gctggggcg atcctcgcca gtctggggtt cgaacagtgc     6540
ataccgctgg tacacggcgc acagggctgt agcgccttcg caaaggtgtt ctttattcaa    6600 catttttcacg acccgatccc gctgcaatcg acggcgatgg atccgacttc caccattatg   6660
ggtgccgatg aaaacatttt taccgcgctc aatgttctct gtcagcgcaa cgccgcgaaa    6720
gccattgtgc tgctcagtac cggcctttca gaagcccagg gcagcgacat ttcgcgggtg    6780
gtgcgccagt tcgtgatga ttttccccgg cataaaggcg ttgcgctgct caccgtcaac     6840
accccggact tttacggctc gctggaaaac ggttacagcg ccgtgctgga aagcatgatt    6900
gaacagtggg tgcctgcgca gcccgccgcc agcctgcgca accgccgcgt caacctgctg    6960
gtcagccatt tactgacgcc gggcgatatc gaactgttgc gcagttacgt tgaagccttc    7020
ggactgcaac cggtaattgt gccggatctg tcgctgtcgc tggacggaca tctggcaaac    7080
ggtgattttt cgcctgttac ccaggggga acatcgctgc gatgattga acagatgggg      7140 caaaacctgg ccaccttggt gattggcaac tcgctgggtc gtgcggcggc gttactggcg    7200
cagcgcagcc gtggcgaggt gatcgccctg ccgcatctga tgacgcttgc agcctgcgac    7260
acgtttattc atcgactgaa aaccctctcc gggcgcgacg tccccgcgtg gattgagcgc    7320
cagcgcgggc aagtgcagga tgcgatgatc gattgccata tgtggttgca gggcgcggct    7380
atcgccatgg cagcagaagg cgatcacctg gcggcatggt gcgatttcgc ccgcagccag    7440
ggcatgctcc ccgcccgat tgtcgcgcg gtcagccagc cggggttgca aaatctgccg      7500
gtggaaaccg tggtcatcgg cgatctggaa gatatgcagg atcagctttg cgcgacgccc    7560
gccgcgttac tggtagctaa ttctcatgcc gccgatctcg ccgcgcagtt tgatctgtcg    7620
cttatccgcg ccgggttccc ggtgtatgac cggctgggag aatttcgtcg cctgcgccag    7680
gggtatagcg gcattcgtga cacgctgttt gagctggcga atgtgatgcg cgaacgccac    7740
cacccgcttg caacctaccg ctcgccgctg cgccagcacg tcgacaatac cgttacgcct    7800
ggagatctgt atgccgcatg ttaatcgtca gttcagcacc atttgccagg gcgaatggtc    7860
aatgaaagtc gcctttgcca gttcggatta tcaccacgtg gatcaacact ttggcgccac    7920
gcccaagtta gtgatctatg gcgtgaaaga gcacgaggtc acgctgttgc gggtggtgga    7980 ttttttctgtg ctcgccggac accagcaaga gaagctcgat tgtcgcattc acgcgctgga   8040
agattgcgtc acgctctact gcgtggcgat tggcgaagcg gttttcgcc agcttttgca     8100
```

```
aatcggcgta cgcgcggttc gcgtgccgca cgcgaccacc attgccgggc tgttgcagga    8160
aattcagcac tactggtatg acaaagagca gcgcaaaagc gcccgcaatc cacaacgctt    8220
cgcccgcatg ctccaggaac aaacctggca ggaagaggat gagcgttagc cacacgccgt    8280
gtcggttgtg tgacaaagcc aacataaaat cgcgacacag cgccgggttt tatgttggca    8340
cattaactta ccccattgaa atgcaacact tttcccttct ggtattgctt ttgcttgatt    8400
gtcatcaccc gccgttgatt gaggcggtga aatgcgccac ggcgctttcc gtcatctctc    8460
ctgggagcca ggcacatgtg gaattactcc gagaaagtga aagatcattt ttttaatccc    8520
cgtaacgcgc gggtggtgga aaacgccaac gccgtgggcg atgtgggctc gttaagctgt    8580
ggcgatgcgc tgcggctgat gctacgcgtg gatccgcaaa gtgaaaccat ccttgaagcc    8640
gggtttcaga cgtttggctg cggcagcgcg attgcctcct cttccgcgct caccgagctg    8700
attattggcc gcacgctggc gcaggccgag caggtgacca accagcagat tgcggattac    8760
cttgatggcc tgccgccgca aaaaatgcac tgctcggtga tgggtcagga ggcgctgcgg    8820
gcggcgattg cccactaccg tggcgaaacg ctgatcgatg agcacgaaga aggcgcgctc    8880
atttgcaaat gctttggcgt cgatgaaggg caaattcgcc gggcggtgct gagtaacggg    8940
ctgaccaccc ttgaagaggt gatcaactac accaaagcgg gcggcggctg caccgcgtgc    9000
catgaaaaaa ttgaactggc gctggccgat attctcgccc ggcacccgca ggccgccact    9060
accgtcactg cggagaaaga tccgcactgg caggaggtcg tcgatgcgat cactgaatta    9120
cgtccgcata tccaggccga tggcggcgat atgtcgctgc ttagcgtcaa caatcacacc    9180
gtaaccgtca gcctttccgg cagttgcagc ggctgcatga tgaccgacat gacgctcgcc    9240
tggctccagc aaaaactgat ggagcgtacc ggctgttata tggacgtcgt ggccgcctga    9300
gccaccactt gtcaaccgat gtgggagaaa atatgaagca ggtctatctg gacaataacg    9360
ccaccacccg tatcgacccg atggtgctgg aagcgatgat gccattctta actgaacatt    9420
acggcaaccc gtcgtcgatt cacgactttg gcacccccte ccgcgccgcg cttgaacgcg    9480
cccgccagca agtcgccgcg ctgctggggg ccgatcacag tagcgaaatc attttcacct    9540
cctgcgcgac cgaggccacc agcaccgcac tgcacgcctg cgttgagctg atgccggagc    9600
gccgggagat tattaccacc gccgttgaac acccggccac tctcgccgtg tgcgaacatc    9660
tggaacgcca gggctacctt atccatcgca ttggtgtgaa tgccagcggc gcactggata    9720
tggaacagta tcgccgcgcg ctgagcacgc gtgtggcagc ggtcagcata atgtgggcga    9780
ataatgaaac cggggtgctg tttccggtga tcgaaatggc ggcgatggcg caggaatatg    9840
gcgcgctgtt tcactgcgat gcggtacaag tggtgggcaa aattccgctg gatatcgccc    9900
gcacgcagat cgatatgctc tcctgctcgg cgcataaact gcacgggcca aaaggtgtgg    9960
gttgcctcta tttgcgccgt ggcacccgct ttcgtccact gctgcgcggt gggcatcagg   10020
agcgcggtcg ccgcgccggt acggagaata tcgccgggat tgtcggcatg ggtgcggcat   10080
gcgaactggc gcagatacac ctgcccggta gcgcgggcat cgccagcctg cgcgatcgcc   10140
tgcaagacga actggtcaaa caggtaccct cagtgatggt gatgggcggc gatcaacccc   10200
gcgttcccgg cacggcgaac ctggcgttcg aatttatcga aggggaagcc atttactgc    10260 tccttaacca ggcggggatc gccgcctcca gcggcagcgc ctgcacctcc ggctcgctgg   10320
aaccgtcgca tgtgatgcgg gcgatgaaca ttccctacac ggcggcgcat ggcagtatcc   10380 gttttttcact ctcgcgctat acgcgggaaa aggagatcga ctatgtaatc gagacgctgc   10440
cagccattat taccogtctg cgcgcgcttt ctccctactg gcaggatggt tctgccccg    10500
```

```
ctacctttgc gccggtttac ggctaaggcg gcgacatgtc cagggttgtg atcaatgaca    10560
ctacgctgcg cgatggcgaa cagagccccg gcgtcgcctt ttgcgccagc gagaaaatcg    10620
ccattgccga agcgctgttt gccgccgggg tgaccgcgct ggaagtcggc accccggcga    10680
tgggccgcga agaacgccag cggatgcgac aagttcgcca gcaactgcct gacgccacgc    10740
tcatggcctg gtgtcgcatg aataccgatg aaatcagcca gagcgccgat ctcggcatga    10800
actgggtgga tatctcacta ccggcttctg acaaactgcg ccagtacaaa ttgcgtgaac    10860
cgctgccggt cgtgctggat aagctggcca cgctgattgc gcaggcgcga cagcagggat    10920
tgcaggtctg tattggttgc gaagacgcat cccgcgccag cgatcggaca ttagcggaga    10980
ttgcccacgt cgcccgcaac gcaggcgcac agcggttgcg ttttgccgat acccttggcc    11040
tgctcgaccc tttcaccacc gctcagcgta tcagcgcgct gcgtcaaagc tggcccggtg    11100
aaatcgaaat gcacgcccat aacgatctcg gtatggcgac cgccaatacg ctggcggcgg    11160
ttcgcgccgg agcaaccagt gtgaatacga ccgtgctggg ccttggcgaa cgcgccggaa    11220
acgccgcgct ggaaaccgtc gcgctcggtc tgagccgctg tctgggtctg gatagcggcg    11280
tggatttcac gcaattaccg atgctctgcc agcaggtcgc cgatgccgcc cggcgtccca    11340
ttgacccaca gcaaccgctg gtaggcgcgc aggtatttac ccatgagtcc ggcgtgcatg    11400
tcgctgccct gctgcgcgat cgcgaaagct accaggccat tgatccggcg ctgatcggcc    11460
gcgaataccg gctggtgctc ggtaagcact ccggtcgtca ggccgtggaa ggtgtattta    11520
cccgcctggg ctatcacctt aatgccctgc aagtcgacct gctgctgccc gccattcgcc    11580
gcgtggcgga aagcagcaaa cgcacgccgc aagacgatga actgattgcg ctttacacca    11640
ccttgtgtgg gtcaggcgcc acacacctgg cgaggggtta aagatggaat ggttttatca    11700
gatccccggc gtggctgaac tcgacagcgc cgagtccttt tttactttt tctccgtgcc    11760 ttatgaaccg ctcacgctgc gccgttgctg cctgccggtg ctgcgcgaat ttcacctgcg    11820
cctgcatgat catgtgccgc tgcgtaatct gcttgaagct acaccccgcg agccctggct    11880
tctggcgcgc aggctgctgg cggaaagcta cgaacactgt acaacggagc cgacatcatg    11940
aaaccaaagt atgcgttcgg tgaggaagtt cgcgttagcc gcgccatccg caacgatggc    12000
accatgccgg gttaccggcg cggcgatttg ctggtgcgtc ggggcagtac gggttttgtc    12060
cgtgaatggg gcacgttcct gatggaaaaa gtgatttatc aaatccactt tcccgactgc    12120
ggtttgattg tgggctgccg cgagcaggaa ctgctgccgc tttccgcccc ctggcacgcc    12180
gggcagttcc agtatggcga taccgtcgcc tgccgccacg cgctggccat cggcgataac    12240
atcgtggtgg ccgccggaga acaaggccag atcgccgcca caggccaggg agacgacgca    12300
gagagttaca ctgtcacctt ttccgggcgc tggtttcagg ttcccgcccg cgccatgatt    12360
ttgctggaga cgccacaatg atgccgtggg agcgtttcgc ccgccgacgg ttggcgctga    12420
cccgctggca ctgcgagccg gaaaacatcc cggcatcaca ccagcaggca tttgaccgcg    12480
cctgggcgcg ccagcgccag ctcgaactgg cagtggttgc cattgcgcgc gacgcaaacg    12540
ttactgacga gctgcgtaat gccgtggccg catcgctggc gccgcagctc gatgagtgcc    12600 cttttttcctc agccgaacgc caggcagtga ttgcgcatca tgcccgtctg gaaacgcagt    12660
ttgctgaggt tgcacgcaca gccccccctcc cggacgaggc gggcgtgctg cgctggtatc    12720
agcaacatca ggcacaattt atgcgcccgg aacagcgctt aacctcgcac ctgctgctga    12780
ccgcagagca aaaccacgcc gggataagaa cacagatcac ccggtttat cagcaaatcc    12840
```

```
gtgaccaccg cgcggccttt ccccggctgg cagcgcgcca ttcgcactgt cccagcgcgc      12900 tggaggggggg cgtctgggc tgggtaagcc gtggcctgct ctttccggaa ctggaaaacg      12960
cgctgtttgc gctgcaaaca gatgaggtca gccagccggt cgaaacggcg ctgggctggc      13020
atttgttgtg gtgtgaacag atccgccaac cggcactgat ggcgaaggca gacgcgctgc      13080
cgaaagcgcg ggagtatttg ttccgtcagt cccaacagca gtggcaacgc cagtggctgg      13140
cgtcattatt acaggcgcgc tga                                              13163

<210> SEQ ID NO 4
<211> LENGTH: 14752
<212> TYPE: DNA
<213> ORGANISM: Methylobacterium L2-4

<400> SEQUENCE: 4
cagggcggcg gccatgacgg cggcgccggt gaaccagggc agcccctcgt agcagagcgc        60
caccgcggcg ttgccccacc agccgttccg cttcagccgc acgggcggcg ccgagtagac       120
ccaggcgagc gcgagcccga acagggcggc cccgaggatc cagggcccga gggcggcggc       180
caccgccagc gacagggccg tccaggcgag ggcgaggtag agccccccagc ggcccgggat      240 ccgcccggac gggatcggcc ggtcggctc gttgatcgcg tcgacgtggc ggtcgaacca       300
gtcgttggcg gcctggctgg tggcgcagac cagcgggccg gccagcagga tgccggcggc       360
gatcaccggc cactggccgc tggccggctg gcccgaggag atgaccccgc aggcgaaggc       420
ccacatcggc gcgaaccacg tgagcggctt cagcagctcg atgactgcgc tcggggcggg       480
cgtagcggtc atggcgggag gctaacgggg cccgcccgga tgtcaagcca gatttacacg       540
acgcgaccac gtgtgcgcga cgtttgtcgg atcaatacag cggcggccca gaaatacatt       600
atccgaaaca cctgggaacc gcggcggcgg accgcccgg cgcgggcggg tcccggcgct        660
ccggcagcgc cccggcggcg ccccgggcgc tccggcgcc cctcggacgc gaggacgatt        720
ccgggatcct cgagccactc ggcgcccggc tcaggcaccc ggttccgggc cgacgcggcg       780
cgcccgcgcg ggctccggc aggcccgggc ggggatgaac cggacgggac ccgcggccgg       840
ccgcgccccg gggcggggggc cgtcaggcct cctcgaccgg gccgtcgagg tcgccgacgc       900
cgtagcggcg catcttggcg tagaggccct gccggctcag gccgagcatc tcggccgccg       960
aggcccggtt gtcccgggtg atccgcagcg ccgcctcgat gcagagcttc tcgatcaggt      1020
ccgtcgtctc gcgcaccagg gtcttcatcg agacccggcc cacgagctcg gtcatctgct      1080
ccaccgagcg gggcacctcc cgaccgaccc gggtcgtcc ctcggcgatc cgccgcgggc       1140
ccgaccggat ggcgaagccc aggcagggc gggtcccggc caccgacacg gcggcgacct      1200
ccacgtcctc catgccgccg taggcgccgc ggacgacggt ggcgaagcgg cgcacggcgc      1260
cgtggtcgac gagggtcgcg aacagcgcct gcgcctcggt ctcgtcgcgg ccgagccagt      1320
ggtcgagggt gcgcccgcgg gcctggccca cggtggcgag ctgcgccagc tccaggaagg      1380
cggcgttggc catcaggacc cgccgcgccg aatcggtgac cacagaagccc tccggcatcg      1440 cctcgatcac cgcggcggtc ggcgcctcct ggtcgggccc ggccgccgcg ccgccgggt       1500 cggcggccag ctgcagcagg gcgctcgcgc cgccctcgcc ccggaacagc gaggccgaga      1560
ccgtgacctc gccgcgcccg tgctggagcg ccgcccggat ctcgcccgcc tgcccggtcg      1620
cccgcagggc ggcgaactgg gcctccaggg tccgggtgct ggcggggtcg aacagctcga      1680
cggcgtcctg cccggcgatg cgcttggccg ggcgcccgag gaggcgggcc gccgccgggt      1740
tggcctcggc cacccggcgc gtgccggcat cgaccaccag caccggctcg ccggagatct      1800
```

```
ggaacagcag ccggtagcgg gtctcggcgg cgcggagccg gtcgtagtcc cgctccaggg    1860
cctgctgggt ctcgaccagc cggcgctgca gggccgccac cgcccgcatg tcgcgcccga    1920
gcacgaggat cgggccgccc tccgagggcc ggatcgacgc gtagcggatc ggcaggtcgg    1980
cgccgtcggg cgagggggtgg ttcacctggc gccagcgggt gatgccctcg gtcccggcat    2040
cccgcagcag ggcgtcgatc ttcgggcggc tctccaccgt gacggtgtcg atccagcgcc    2100
ggcccagcca gccggccacg gtctcggccg cgaggtcggc gccgaccgcg cgtcccgaa    2160 tcaccccgtc ggcgtcgatc accagggaga ggtccgcgga cgccgcgacg atgcgcccga    2220
ccgcctcgcc ctggaggagg ccggccacct gctgcagggc cgcgggcggc gactgcgggg    2280
aggggcgggg ctgaggggtc acggtcaccg caatgtgata gtcggtttga ggcccttca    2340 gcaggccaat gcctgtctgt ccagcaaagc ttccgccgcg gcgggcgcga ggcacgcgtc    2400
cgacgcgcag gcatccgccc cgacgatccc cgcctcgccg ccgtggcgcg cgaagaaggg    2460
gccgccgacc agcaccccgga cgtcccggtt gcgcgagtcg cggcgcacct ccgccaccgt    2520
cgccgtcagg accggcagca ggacgtcgca ggagagcgac aggccgacca cgtcgaacca    2580
gtccgaccgg agcaggtcca gggggtcgac ccccggcccg ggcaccgcgg tggtcacgtc    2640
ccagccggcc tcccggaaga agctcgcgac cagggacagg ccgaagacgt gggtctcgcc    2700
cgggcagggc agcagcagga cgctgcgccc gatggccggg accgattcgc tctccagctc    2760
ggcgcagagg cggcggctca cggcgtggag ccgcccgagg gcctcggtca ccgccaggaa    2820
gtcgcaggca tcctcctccc agagggcgcc gagatgccgg gccgccgggg cgagcaggtc    2880
gaggagcagg cgcgcgagcg gcaggccgcc gtcgcgcagg gcgtccaccc gggcgtcgag    2940
gtcgaccggg ccggcggcca ggagcagggc gctgaaatcg gcgatctccc gcgcgctcgg    3000
cgcccggtcc gccgggacgg cgcggccggc gggccggtgg gcgagcatca ggcggggcag    3060
gatctccgcc tcgacgacct tggcgagcgc gtccggacg ggcctgtgca ggtcggacca    3120
accgagggca gtgtcgcgga acacgggaag accatcgctc acggggctgc agccggccgc    3180
ggacggaccg taatcaagac ggccaccgaa atgcctccag tttcccatcg gcatcctccc    3240
tgagacgacc ccgcccgga agggccggcg gatccgctcg cctgctcggt gcggcgttgc    3300
tcgcccgtct attcttcgcg tccgccagtt cctggatctg acaagccaaa cggcggcaat    3360
ctctgccgtc tcagttgacg atacgcttcc tggccatctt ggcaatgatc ttattcgaag    3420
aaaaaatatc cctccccgtg tcaaaccaca gaagcgtcaa gcgcacttga cacttccggg    3480
acccccgccc tagcctctgt caacgacgga gcctctggcg ccgccgacca gcagggagcg    3540
gatgcatggg tcccgaggac cggccggcac gaccgctcta cacgctcgcc gaacggcgcc    3600
ggcgcgattc ctcgccctgg accctggtcc agggggttct ggcgcccctc cagttcgcga    3660
tcttcctgat cagtctcgcc ctggtgctgc gtgccctggc caccggtgac ggcgcgcgcg    3720
cggccgagat ctcggtcgtc gtgaagaccg tggccctcta cgccgatcatg gtcaccggtt    3780 cgatctggga gaaggtcgtg ttcggacggt ggctcttcgc acccgccttc ttctgggagg    3840
acgtggtcag catgctggtg ctggccctcc acaccgtcta cctcgcggcc ctcgcgacgg    3900
gcgccctgag cgggcaggcg ctgctgctcc tcgcgctggc ggcctacgcg acctacgtgg    3960
tcaacgcggc ccagttcctt ctgaagctcc gggccgcgcg cctggagggg gccggcagcc    4020
gcgcaccgcg tctcgcggag gcgctgccat gaacgcccc ctggcccacc cgccgccctg    4080
cggcggcatc gaactgcgcc aggagcacgg ccagcggggcc gtgttctgcg gcctcaccgg    4140
```

```
catcgtctgg ctgcaccgga agatccagga cgcgttcttc ctcgtggtcg gctcgcgcac    4200
ctgcgcgcac ctgatccagt cggcggccgg ggtgatgatc ttcgccgagc cgcgcttcgc    4260
caccgccatc atcgacgagc gcgacctcgc cggcctcgcc gacgccaacg aggagctcga    4320
ccgggtggtg acccggctga tcgagcgccg gcccgacatc aagcttttgt tcctcgtggg    4380
ctcctgcccg tccgaggtga tcaagctcga cctgtcccgg gcggcgcagc gcctgtcggg    4440
ccgcctcgcc cccgtgcggg tgctgaacta ttcgggctcc ggcatcgaga cgaccttta c    4500 gcaaggtgag gatgcctgcc tcgcggcgct ggtgccggac ctgccccgcg aggcagaggc    4560
aaccgcgtcg tcgctcctga tcgtcggggc gctggccgac gtggtggagg accagttcct    4620
gcggatgttc gccgcgatgg gcatcgcgga tgtccggttc ctgcccgccc gccgggccgg    4680
cgccatgccg gcagtcgggc gcggcacccg ctacctgctg gcccagccct tcctgaccga    4740
gaccgcccgc gccctcgagg aacgcggcgc ccgccggctc gcggccccgt tcccgctcgg    4800
cgccgagggc accaccggct ggctgcgggc cgccgccgag gcgttcggcg tctccgggga    4860
ggcgttcgac cgggcgaccg ccgcgggccg ggcccgcgcc gagaccgcgc tcgcgcccca    4920
ccgcgagaag ctcggcggca gcgggtgtt cttcttcccc gactcgcagc tagaggtgcc    4980
gctcgcccgc ttcctcgccc gggaactcgg cgctgagctc gtggaggtcg ggacgcccta    5040
cctgcaccgg ggacatctcg ccgccgagat cgagtggctt cccgcgggca cacgcgtgac    5100
cgagggccag agcctcaacg accagatgga ccgctgccgg gcggcccgcc cggacctcac    5160
ggtctgcggc ctcggcctcg ccaacccgct ggaggcggag gggctgtcga ccaagtggtc    5220
gatcgagttg ctgttcacgc cggtgcaggg ctacgagcag gccggcgacc tcgccgagct    5280
gttcgtgcgc ccgctccgac gccgtgccct gctggaggtg tagcgccatg cagctcaccc    5340
tctggaccta cgagggcccg cctcacatcg gcgcgatgcg cgtcgccacg gcgatgtccg    5400
ggctgcatta cgtgctgcac gctccgcagg gcgacaccta cgccgacctg ctgttcacca    5460
tgatcgagcg gcggggcgcc cgcccgcccg tgacttacac gaccttccgt gcccaggatc    5520
tcggccgcga caccgccgag ctgttcaagg aggcggtcgc cgccgcgcac gcacggttcc    5580
ggccccaggc catgatcgtc ggcgcctcct gcacggccga gctgatccag gacgatccgg    5640
gcggcctcgc caaggccctc gaccttccga tcccggtgat cccgctggag ctgcccgcct    5700
accagaagaa ggagaactgg ggcgcgtcgg agaccttcta ccggctggtc cgcgcgctcg    5760
ccggggctcc ggccccgcgc ccggcgcggg agcccgggcg gcgcccgctc tgcaacattc    5820
tgggttcaac ggcgctgggc ttccgccacc gggacgacct gatcgagatc cgccagctgc    5880
tcgataccct cggcatcgcc gtgaatgtcg tggcgccgct gggggccacg cccgccgatc    5940
tgggccggct ccgggacgcc gacttcaacg tcgtgctcta tcccgagacg gcccgctccg    6000
ctgcggacta cctgaagaag gccttcgggc agccgttcac gcaaaccatc ccgatcggcg    6060
tcggcggcac ccgccggttc gtcgaggagg tggcgggcct cgccgggatt gaccggcgc    6120 cggtgctcga cggatccggc tcgcggctgc cctggtactc ccgctcggtc gattcgacct    6180
atctcacggg caagcgcgtc ttcgtgttcg gcgacgccac gcacgccatc ggcatcgccc    6240
gggtcgccgc gaaggaactc ggcttcaccc tcgtcgggct cggcacctac ggccgcgagt    6300
tcgcccgcga ggtccgcgcc gaggcggccg agcacggtat cgaggcgctg gtcaccgacg    6360
actacctcga cgtcgaggcg gcgatccgcg cggccgcgcc ggaactcgtc ctcggcaccc    6420
agatggagcc ccacgtcgcc aagcggctcg gcatcccctg cgcggtgatc tccgcgccgg    6480
tccacgtcca ggacttcccg gcgcgctacg ccccgcagat gggcttcgag ggcgccaacg    6540
```

```
tcctgttcga caccctggtc catccgctga tgatgggcct cgaagagcac ctcctcggca    6600
tgttccggga agatcccgaa ttccacgacg gcgtcggccc ctcgcatctc ggcggcaagt    6660
ccttcgggac tccggcggac gaggcgttcg aggccgcgga acgggcgccg gctgacaccc    6720
ctccgacgcc ggcgcccgtt ccgatcctgc ttgagcggcc ggccgcgacc gcgtggtcgc    6780
ccgaggccga aaggagctg aagaagatcc cgttcttcgt gcggggcaaa gcacgcacga    6840
acaccgagac tttcgcgcgg gagcggcacc tgccgctcat caccctcgag accctctacg    6900
atgccaaagc gcattacggc cgctaggccg ccgatccgcg tcgtcatcgt cacgctcgac    6960
aatcacttgg cgagcgcggt ggagcgggcg cgcctgcgcc tccggtccga gatgcccggg    7020
ctggtgctgg gcttccacgc ggccgccgag tgggacaacg atcccgcgac gctggcggcc    7080
tgtcgggccg acatcgcgca ggccgacatc gtgctctcgg ccatgctgtt catgacgag    7140 cacgtgcggg cgatcctgcc ggcgctggcg gcccggcgcg cggcctgcga cgcgatggtc    7200
ggctgcctct cggccggcga ggtggtgaag accacgaagc tcggccgctt cgacatgagc    7260
ggcaccaagc gcagcgccct cgacttcctg aagaagctgc ggggcaagcc gggccagcag    7320
ggcaatgccg gccggcagat ggccctggtg cgcaaactgc cgaagatcct gcgcttcatc    7380
ccgggttcgg cccaggacgt gcgcgcctat ttcctgaccc tgcaatactg gctggcgggc    7440
tcggacgaga acgtcgccgc gctggtgcgc ttcctcgtgc accgctacgc ggccggcgag    7500
cgcgccgcct ggcgcgaggg tccggcggcg ccggcacccc tcgattatcc ggagacaggt    7560
ctctaccacc cgccgcctcat cggtcggatc ggtgccgacc cgtcgcggct gccgcgcctc    7620
acgggcgcca agggccgggt cggcctgctg gtgatgcgca gctacgtgct cgccggcaac    7680
accgcccatt acgacggcgt catcgccgcc ctggaggcgc ggggcctcga cgtggtgccg    7740
gccttcgcca gcggcctcga caaccgcccg gcggtagagt ccttcttctt ggaggacggg    7800
cgcgccagca tcgacgcgct ggtctcgctc accggcttct cgctggtcgg cggccccgcc    7860
tacaacgacg ccgccgccgc cgaggcgatg ctggcccggc tcgacgtgcc ctacctcgcc    7920
gcccaggcgc tggaatttca gaccctggaa cagtgggagg cgggtgaccg cggcctgtcg    7980
ccggtcgagg cgaccatgat ggtcgcgatc cccgaactcg acggcgccac cacccccgacg    8040 gtgttcggcg gccgctccgc cgaattccggc gccgacaacg caagggacat gcgggtccat    8100
cccgagcgcg cggcccggct cgccgagcgg gtcgcgcgac tggtatcgct ccgccggacc    8160
gcgaaggccg agcggaagct cgccgcggtg ctgttcaact tcccgcccaa tgccggcgcc    8220
accggcacgg cggcgttcct gtcggtctac gcctcgctgc tcaacacgct gaagggcctg    8280
gcggcggacg gctacacggt cgaagtgccg gagagcgtcg acgccctgcg cgaaaaaatc    8340
ctcgacggca atgccaagcg ctacggcacc caggccaacg tccacgcccg cattccggcc    8400
gaggaccacc tgcgccgcga gccctacctc gcggagatcg aggcccagtg gggcccggcg    8460
ccgggccgcc accagaccaa cggcgccgac atcttcgtgc tgggcgcgca gttcggcaac    8520
gtcttcgtcg gggtccagcc cgccttcggc tacgagggcg acccgatgcg gctgctgttc    8580
gagcgcggct tcgcaccgac ccacgcgttc agcgccttct accgctacct gcgcgaggac    8640
ttcagcgccc acgccgtgct gcatttcggc acccacgggg cgctcgagtt catgcccggc    8700
aagcagaccg gcctgtccga atcctgctgg ccggagcggc tgatcggggc gctgcccaac    8760
gtctacctct acgcggccaa caacccgtcc gaggggacgc tcgccaagcg cgcgctcggcg    8820 gcgacgctgg tgagctacct gaccccgagc ctcgcggcgg ccggactcta tcgcggtctg    8880
```

```
ctcgacctga agagctcgat cgagcgctgg cgcggcctcg gccccgaggc gggcggcgag    8940
cgcgagacgc tggcgcgcct gatccaagac cagggcgcgg cggtcgatct cgtcgccgcc    9000
gagccggcct ggaccggcga tctggaggct cgggtctccg gcctctggac cgcgctgcag    9060
gagctggagc agaccctgat cccgcacggc ctgcacgtgg tcggcgcggg cacgccggaa    9120
gaggagcggg tcgatctgct cctggcgctc gcccagtcgg cgcacggcgt gcggccggag    9180
cgggccggga tcgaggccct cgtcacgggg caggggtcg aggcggcgct gacggcttcc    9240
ggcctgcccg ccgacgacgt gacccgggcg gcgttcgcaa gtctggcgga gaccgaccgg    9300
ctgctgtcgc gcgaccacga ggttccggcg ctgctgcggg cgctggacgg ccgcttcgtg    9360
ccgccggtgg ccggcggcga cctgctgcgc aacccggccg tgctgccgac aggccgcaac    9420
ctccacggct tcgatccgta ccgcctgccc tcggccttcg cggtggcgga cggtgcccgg    9480
caggtggccc gcatcctcga acgcttcgcc gcggacggaa aaccctgccc ggagagcgtc    9540
gccctggtcc tgtggggcac cgacaatctc aagagtgagg gcggcccgat cgcccaggct    9600
ctggcgctga tcggcgccgc gccccgcttc gacggctacg ggcgcctgag cggcgccgag    9660
ctgatcccgc tggagaccct cggccgcccg cggatcgacg cggtggtgac cctctcgggc    9720
atctttcgag acctgctacc gctgcagacc aaactcctgg cggaagcgtc tttcctcgcc    9780
gccaccgccg acgagcccct cgaacagaac tacgtccgca agcacgccct cgcgatccag    9840
gccgagcagg gctgcgatct ggagacgcg gcgctccggg tcttctccaa cgccgagggc    9900
gcctacggag ccaacgtcaa tcacttggtc gactcgggca actgggacga cgaggccgag    9960
ctctgcgaga ccttcgcgcg ccgcaagagt ttcgcctacg gccgcaccgg ccgcccggcg   10020
ccgcagcggg cgctgatgca ggcggtgctc gcctccgtcg acatggccta ccagaacctc   10080
gactcggtcg aggtcggcgt cacctcggtc gaccactact tcgacgggct cggcggcatg   10140
ggccgggcgg tggcccgggc caagggcgag tcggtgccga tctacatcag cgaccagacc   10200
cgcggggagg ggcgcgtccg ctccctggag gagcaggtgg cgctggagac gcgcacccgg   10260
atgctcaacc cgaaatggta cgagggcctg ctcggccacg gctacgaggg cgtccggcag   10320
atcgagacgc atctcaccaa cacggtcggc tggtcggcca ccgccaacgc ggtccagccc   10380
tggatctacg agcggatcac cgagacctac gtcctcgacc ccgccatgcg cgagcgcatg   10440
gccgccttga cccccaccgc ctccgccaag gtcgcccaga ggctgatcga ggcgcaccgc   10500
cgcggcttct ggaccccga cgcagcgatg cgcgacgccc tcgaccgggc cgaggaggag   10560
ctggaggacc gcctggaagg cgtcaccgca ggagtggccg catgaacatc gcgatccgca   10620
accccgtcgt ggcgcgaaag gaggagggga gccttcaggt cgccctcgat cccgatctga   10680
agatcgagac cgccaaggtc ttcgcggtct acggcaaggg cgggatcggc aagtcgacca   10740
cctcgtcgaa cctgtcggtg gccttctcga agctcggcaa acgggtgctg cagatcggct   10800
gcgacccgaa gcacgattcg accttcacgc tgaccaagcg cctcgccccc acggtgatcg   10860
acgcgcttga ggcggtgaac ttccactcgg aggagctgcg cgtcgaggat ttcgtggtcg   10920
agggctacaa cggggtgatg tgcgtcgagg ccggcggccc gccgccggc accggctgcg   10980
gcggctacgt ggtcggccag acggtgaagc tcctcaagga gcaccactc ctcgaagaca   11040
ccgatgtcgt cgtgttcgac gtgctgggcg acgtggtctg cggcggcttc gcctcgccgc   11100
tccagcacgc cgaccgggcg ctgatcgtca ccgccaacga cttcgactcg atcttcgcca   11160
tgaaccggat cgtcgcggcg atccacgcca agtccaagaa ttacggcgtg cgactcggcg   11220
gcgtcatcgc caaccgctcg gccaagaccg acgagatcga ccggttcaac gacgcggtcg   11280
```

```
gcctgaagcg gctggcgcat ttccccgacc tcgacgtggt ccgccgctcg cggctcaaga   11340
agtcgaccct gttcgagatg gagtcctcgc cggagctcga cgccgtgacc gccgagtaca   11400
tgcggctcgc cgagacgctc tgggccggcg ccgagccctg cgaggcgcag cccatgaagg   11460
accgcgacct gttcgagttt ctgggattcg actgatggcc agcgccagct acgacgcccg   11520
ccggggcgag ctgaccacct acttcgaccg caccgcggtc gaggcgtggt cgcgcctgac   11580
ctcggacgcg cccgtgagcc ggatccgcgc acggtgcgg gccgggcgcg acgccatgcg   11640
ggccacgctg ctctcctggc tcccggccga catgaccggc ctgcgtttgc tcgatgccgg   11700
ctgcggcacc ggggcgctca gcgtcgaggc ggcgcggcgc ggcgccgagg tggtggcgat   11760
cgacgtctcg ccgacgctga tcgggctggc gcaggagcgg ctgccggcga tcgccggcgc   11820
ggggcgcatc gatttccggg tggcgacat gctcgatccc gggctcgggc ggttcgatca   11880
cgtggtggcg atggattcgc tgatccacta ccgcgccgcc gacatcgccc gggcgctggc   11940
ggtcctgggt gcgcgcacgg acgggtcggt gctgttcacc gtggcgccgc gcacggccct   12000
gctgacgctg atgcacgcgg ccggaaaatt cttcccgcgc ggcgaccgct cgccttccat   12060
cgtgccggtg accgagggtg gattgcggcg gcggatcgcc tcggagagcg ccctggacgc   12120
cttcgcctgg gcgcagagcc accggatcaa cagcgggttc tacctgtcga acgcggtggc   12180
gctgacacgc accctgccgc cccgcgcgga tcggggcggg ggcccggtgc aatccgggat   12240
gcggccatga ccccacccg caagctcacc gccgccctga tgcgcctcgg cccggcggtg   12300
ctgcccttcg cggacgccgc caccgccgag ctgccgctcg gcggctgct ccgcctcgcc   12360 ctgttccagg tcaccgtcgg catggccgcg gtgctgctga tcggcaccct gaaccgggtg   12420
atgatcgtcg agctcggcgt cccggcctgg atcgtggcga tgatgctggc gctgccgctg   12480
gtcttcgccc ccttgcgggc gctggtcggc ttccgctcgg acacgcaccg ctcggtgctg   12540
ggctggcggc gcgtgcccta catctggttc ggcacgctgc tccagttcgg cggcctcgcg   12600
atcatgccgt tcgccctgct catcctgtcg ggcgacacga ccgggccgct ctgggtcggc   12660
gacctcgcgg cggcgctcgc cttcctgctg tcggcgcgg gcctgcacac gacccagacc   12720
gtggggctcg ccctcgccac cgacctcgcc cccgcccatg cgaggccgaa ggtggtggcg   12780
ctgctctgcg cggccctgct gttcggcatg atggcgagcg cggtgctgtt cggcctgttc   12840
ctggcccatt tctcgcccgt ccggctgatc caggtgatcc agggcgcggc cctcgtcacc   12900
atcatcctca acgggttcgc cctgtggaag caggagccgc gcgatccgaa ccggacgcgg   12960
acggcgccgc agcgggactt ccggtcctcc tggcgggcct atgcggggca gggcaccgcc   13020
cggcgccgcc tcgtggcgat cgggctcggc acggcgggct tctccatgca ggacatcctg   13080 ctcgaacccct acgcggcca gatcctgcac ctctcggtgg cggccaccac ggcgctgacc   13140
gccttgctgg ccgccggtgg cgggctcggc ctgctggtcg cggcgcgctg gctcggccgc   13200 ggggcgacc cgttccgcgt ctccgcggtc ggcgtcggga tcgggatcct cgcgttctcg   13260
gcggtcgtgt tcgccgcccc gctcgcctcg ccgacctgt tcgccgcggg cgtgagcctg   13320
atcgggctcg gcggcggcct gttcgcccac ggcaccctca ccgcctcgat gaaccgggcc   13380
ggccccgagg ataccgggct cgcgctcggc gcctggggcg ccgtgcaggc gaccgcgcc   13440 ggcctctcga tcgcggcgag cggcctcgtg cgcgacgtgg cggcgccat cgcccagtcg   13500 ggggtgctgg gcgagggcat gaacgagccg gccatcggct acctcatcgt ctaccacatc   13560
gagatcgccc tgctgttcgc cgcgctgctc gcgctcggac cgctggtgcg cgaggacgct   13620
```

-continued

```
cggacagagg atcggaaccg catcgccgac ggccttgccg gccggacggc ctgacattcg    13680
gggaggacag ccatgccaac cggcgcactt acggggttacg tcgacgtcgc ccaggtcgtg    13740
ctctacgcct tcttcctctt cttcgcggga ctggtcttct ggctccgccg cgaggaccgg    13800
cgcgagggct atcccctgga gaacgaggcg gtcggccggc gcaaggcgga cgacccgatc    13860
ctgatcccgc ggtccaaggc gtttcacctg ccgggcggcg agacgaccta cgcgccgcag    13920
gcggtgcacg gccgggacga catcgagacc ggcatcccgg cccgcaaggt cgagccctgg    13980 ccggggggcgc cctacgagcg cacggaatcg tcgctccagg ccggcgtcgg tcccggctcc    14040
tgggtgctgc ggcacgacgt gcacgaccgg acctgggacg acgagatccg catcgtgccc    14100
ctccgggtgg cgaagaactt cgtcatccac gaggacggcc cgaacccgat cggcatgacg    14160
gtgttcggca ccgacagcgc cgtcgcgggc gtgatcagcg acgtctgggt cgaccgcggc    14220
gagtcgctga tccgctacta cgaggtcgag ctcccgacgg gcggacgccg gctgatgccg    14280
accacgttct gccgggccgg cggttttcacc aagacggtga cgaccgaggc gctgctcgcg    14340
agccagttcg ccgacatccc gaccaccgcc gatcccgaca gcgtaaccctt cctggaggag    14400 gagcggatca tctcgtattt cggcgccggc acgctctacg cgacgccggc ccgggcggag    14460
cccctgatat gagcggcgac ttcctccccg aaggcaccct gcggggtctg cccggccgc    14520 tgccgccggg cgagcgcatc ctctggcagg gcgcgccgac caccgcgggc ctgctggtcc    14580
gagtgttcca cgcccgcctc gtgatcgcgt ggttctcggt ctgcgccctg ccttcggcc    14640 tcgcggcggg ctcgcccgcg gcggcgctga gggtggtggc gccgacccctg gtgatcggcg    14700 ccggcgccgt cgcgctgctc tggctgctcg cctggctcac ccaccggacg ac             14752
```

<210> SEQ ID NO 5
<211> LENGTH: 40
<212> TYPE: DNA
<213> ORGANISM: Enterobacter sp R4-368

<400> SEQUENCE: 5

```
cgttaatctc aatttggctc agcatcaaac agtttggtat                            40
```

<210> SEQ ID NO 6
<211> LENGTH: 35
<212> TYPE: DNA
<213> ORGANISM: Enterobacter sp R4-368

<400> SEQUENCE: 6

```
gcgttggccc aggggatgtg ctgaacgtaa ccgtg                                 35
```

<210> SEQ ID NO 7
<211> LENGTH: 31
<212> TYPE: DNA
<213> ORGANISM: Enterobacter sp R4-368

<400> SEQUENCE: 7

```
ccccgcaggt gctgtatcgc tggcgcgcat t                                     31
```

<210> SEQ ID NO 8
<211> LENGTH: 31
<212> TYPE: DNA
<213> ORGANISM: Enterobacter sp R4-368

<400> SEQUENCE: 8

```
ctggtgctgc gttcccgcga ggagctgaac c                                     31
```

<210> SEQ ID NO 9
<211> LENGTH: 32
<212> TYPE: DNA
<213> ORGANISM: Enterobacter sp R4-368

<400> SEQUENCE: 9

```
cgtctgaacg ttgaatcgcg gcacgacgag ga                                    32
```

<210> SEQ ID NO 10
<211> LENGTH: 1740
<212> TYPE: DNA
<213> ORGANISM: Enterobacter sp R4-368

<400> SEQUENCE: 10

```
gcacctgctc tttaacaatt tatcagacaa tctgtgtggg cactcagggt gactggattc      60
ttgacgtcgc aagacgaaaa atgaatacca agtctcaacg agtgaacacg taattcatta     120
cgaagtttaa ttcattgagc atcaaacttt taaattgaag agtttgatca tggctcagat     180
tgaacgctgg cggcaggcct aacacatgca agtcgaacgg tagcacagag agcttgctct     240
cgggtgacga gtggcggacg ggtgagtaat gtctgggaaa ctgcctgatg gagggggata     300
actactggaa acggtagcta ataccgcata acgtcgcaag accaaagagg gggaccttcg     360
ggcctcttgc catcagatgt gcccagatgg gattagctag taggtggggt aacggctcac     420
ctaggcgacg atccctagct ggtctgagag gatgaccagc cacactggaa ctgagacacg     480
gtccagactc ctacgggagg cagcagtggg gaatattgca caatgggcgc aagcctgatg     540
cagccatgcc gcgtgtatga agaaggcctt cgggttgtaa agtactttca gcggggagga     600
agggagtaag gttaataacc ttattcattg acgttacccg cagaagaagc accggctaac     660
tccgtgccag cagccgcggt aatacggagg gtgcaagcgt taatcggaat tactgggcgt     720
aaagcgcacg caggcggtct gtcaagtcgg atgtgaaatc cccgggctca acctgggaac     780
tgcatccgaa actggcaggc ttgagtctcg tagaggagg tagaattcca ggtgtagcgg     840
tgaaatgcgt agagatctgg aggaataccg gtggcgaagg cggcctcctg gacgaagact     900
gacgctcagg tgcgaaagcg tggggagcaa acaggattag ataccctggt agtccacgcc     960
gtaaacgatg tctatttgga ggttgtgccc ttgaggcgtg gcttccggag ctaacgcgtt    1020
aaatagaccg cctggggagt acggccgcaa ggttaaaact caaatgaatt gacggggggcc    1080
cgcacaagcg gtggagcatg tggtttaatt cgatgcaacg cgaagaacct tacctggtct    1140
tgacatccac agaactttcc agagatggat tggtgccttc gggaactgtg agacaggtgc    1200
tgcatggctg tcgtcagctc gtgttgtgaa atgttgggtt aagtcccgca acgagcgcaa    1260
cccttatcct ttgttgccag cggttaggcc gggaactcaa aggagactgc cagtgataaa    1320
ctggaggaag gtggggatga cgtcaagtca tcatggccct tacgaccagg gctacacacg    1380
tgctacaatg gcgcatacaa agagaagcga cctcgcgaga gcaagcggac ctcataaagt    1440
gcgtcgtagt ccggattgga gtctgcaact cgactccatg aagtcggaat cgctagtaat    1500
cgtggatcag aatgccacgg tgaatacgtt cccgggcctt gtacacaccg cccgtcacac    1560
catgggagtg ggttgcaaaa gaagtaggta gcttaacctt cgggagggcg cttaccactt    1620
tgtgattcat gactggggtg aagtcgtaac aaggtaaccg taggggaacc tgcggttgga    1680
tcacctcctt accttaaaga acctgcctct gcagtgtcca cacagattgt ctgatgaaaa    1740
```

<210> SEQ ID NO 11
<211> LENGTH: 1443
<212> TYPE: DNA

<213> ORGANISM: Pleomorphomonas jatrophae R5-392
<220> FEATURE:
<221> NAME/KEY: misc_feature
<222> LOCATION: (603)..(603)
<223> OTHER INFORMATION: n is a, c, g, or t

<400> SEQUENCE: 11

```
gagtttgatc ctggctcaga acgaacgctg gcggcaggct taacacatgc aagtcgaacg      60
ctcgcagcaa tgcgggagtg gcagacgggt gagtaacgcg tgggaacata ccctttggtt     120
cggaataact gagagaaatt tcagctaata ccggatgtgc cctatggtgg aaagatttat     180
cgccaaagga ttggcccgcg tctgattagc tagttggtga ggtaacggct caccaaggcg     240
acgatcagta gctggtctga gaggatgatc agccacactg gactgagac acggcccaga      300
ctcctacggg aggcagcagt ggggaatatt ggacaatggg gcaaccctg atccagccat       360
gccgcgtgag tgatgaaggc cttagggttg taaagctctt tcgtcaggga agataatgac     420
ggtacctgaa gaagaagccc cggctaactt cgtgccagca gccgcggtaa tacgaagggg     480
gctagcgttg ttcggaatta ctgggcgtaa agcgcacgta ggcggacatt taagtcaggg     540
gtgaaatccc agggctcaac cctggaactg cctttgatac tgggtgtctt gagtacgaga     600
gangtgagtg gaattccgag tgtagaggtg aaattcgtag atattcggaa gaacaccagt     660
ggcgaaggcg gctcactggc tcgtaactga cgctgaggtg cgaaagcgtg gggagcaaac     720
aggattagat accctggtag tccacgcgtgt aaacgatgaa tgccagccgt tgggcgacgt     780
gtcgttcagt ggcgcagcta acgctttaag cattccgcct ggggagtacg gtcgcaagat     840
taaaactcaa aggaattgac gggggcccgc acaagcggtg tagcatgtgg tttaattcga     900
agcaacgcgc agaaccttac cagcccttga catccgtcga ccgtggaga gatccatttt       960
gcccttcggg gccggcgaga caggtgctgc atggctgtcg tcagctcgtg tcgtgagatg    1020
ttgggttaag tcccgcaacg agcgcaaccc tcgccttcag ttgccagcat ttggttgggc    1080
actctggagg gactgccggt gataagccgg aggaaggtgg ggatgacgtc aagtcctcat    1140
ggcccttacg ggctgggcta cacacgtgct acaatggcgg tgacaatgag cagcgacttc    1200
gcgaggagaa gctaatctca aaaagccgtc tcagttcgga ttgcactctg caactcgagt    1260
gcatgaagtc ggaatcgcta gtaatcgcgt aacagcatga cgcggtgaat acgttcccgg    1320
gccttgtaca caccgcccgt cacaccatgg gagttggctt acccgaagg tagtgcgcta     1380
accgcaagga ggcagctaac cacggtaggg tcagcgactg gggtgaagtc gtaacaaggt    1440
aac                                                                   1443
```

<210> SEQ ID NO 12
<211> LENGTH: 1414
<212> TYPE: DNA
<213> ORGANISM: Sphingomonas sp. S6-274

<400> SEQUENCE: 12

```
acgaacgctg gcggcatgcc taacacatgc aagtcgaacg agagcttcgg ctctagtggc      60
gcacgggtgc gtaacgcgtg ggaatctgcc cttgggttcg gaataacagt tggaaacgac     120
tgctaatacc ggatgacgtc gataagacca aagatttatc gcccgaggat gagcccgcgt    180
cggattagct agttggtggg gtaaaggcct accaaggcga cgatccgtag ctggtctgag     240
aggatgatca gccacactgg gactgagaca cggcccagac tcctacggga ggcagcagtg    300
gggaatattg gacaatgggc gcaagcctga tccagcaatg ccgcgtgagt gatgaaggcc    360
ttagggttgt aaagctcttt tacccgggaa gataatgact gtaccgggag aataagcccc    420
```

```
gggctaactc cgtgccagca gccgcggtaa tacggagggg gctagcgttg ttcggaatta        480
ctgggcgtaa agcgcacgta ggcggctttg taagtcaggg gtgaaagcct ggagctcaac        540
tccagaactg cctttgagac tgcatcgctt gaatccggga gaggtgagtg gaattccgag        600
tgtagaggtg aaattcgtag atattcggaa gaacaccagt ggcgaaggcg gctcactgga        660
ccggtattga cgctgaggtg cgaaagcgtg gggagcaaac aggattagat accctggtag        720
tccacgccgt aaacgatgat aactagctgt ccgggaactt ggttttgggg tggcgcagct        780
aacgcattaa gttatccgcc tggggagtac ggccgcaagg ttaaaactca aggaattga         840 cgggggggcct gcacaagcgg tggagcatgt ggtttaattc gaagcaacgc gcagaacctt        900
accagcgttt gacatgtccg gacgattccc agagatgggt ctcttccctt cggggactgg        960
aacacaggtg ctgcatggct gtcgtcagct cgtgtcgtga tgttgggt taagtcccgc         1020 aacgagcgca accctcgcct ttagttacca tcattgagtt gggtactcta aggaaccgc         1080 cggtgataag ccggaggaag gtggggatga cgtcaagtcc tcatggccct tacgcgctgg       1140
gctacacacg tgctacaatg gcgactacag tgggctgcaa tcccgcgagg gtgagctaat       1200
ctccaaaagt cgtctcagtt cggattgttc tctgcaactc gagagcatga aggcggaatc       1260
gctagtaatc gcggatcagc atgccgcggt gaatacgttc ccaggccttg tacacaccgc       1320
ccgtcacacc atgggagttg ggttcacccg aaggcgttgc gctaactcag caatgagagg       1380
caggcgacca cggtgggctt agcgactggg gtga                                   1414
```

<210> SEQ ID NO 13
<211> LENGTH: 1409
<212> TYPE: DNA
<213> ORGANISM: Methylobacterium L2-4

<400> SEQUENCE: 13

```
agatcaatct cttcaacgtg agagtttgat cctggctcag agcgaacgct ggcggcaggc         60
ttaacacatg caagtcgagc gggcccttcg gggtcagcgg cggacgggtg agtaacgcgt        120
gggaacgtgc cttctggttc ggaataaccc tgggaaacta ggctaatac cggatacgcc         180 cttttgggga aggtttact gccggaagat cggcccgcgt ctgattagct agttggtggg         240
gtaacggcct accaaggcga cgatcagtag ctggtctgag aggatgatca gccacactgg         300
gactgagaca cggcccagac tcctacggga ggcagcagtg gggaatattg acaatgggc         360 gcaagcctga tccagccatg ccgcgtgagt gatgaaggcc ttaggggttgt aaagctcttt        420 tatccgggac gataatgacg gtaccggagg aataagcccc ggctaacttc gtgccagcag        480
ccgcggtaat acgaaggggg ctagcgttgc tcggaatcac tgggcgtaaa gggcgcgtag        540
gcggcgtttt aagtcggggg tgaaagcctg tggctcaacc acagaatggc cttcgatact        600
gggacgcttg agtatggtag aggttggtgg aactgcgagt gtagaggtga aattcgtaga        660
tattcgcaag aacaccggtg gcgaaggcgg ccaactggac cattactgac gctgaggcgc        720
gaaagcgtgg ggagcaaaca ggattagata ccctggtagt ccacgccgta aacgatgaat        780
gccagctgtt ggggtgcttg caccgcagta gcgcagctaa cgctttgagc attccgcctg        840
gggagtacgg tcgcaagatt aaaactcaaa ggaattgacg ggggcccgca caagcggtgg        900
agcatgtggt ttaattcgaa gcaacgcgca gaaccttacc atcctttgac atggcgtgtt        960
acccagagag atctgggtc cccttcgggg gcgcgcacac aggtgctgca tggctgtcgt       1020
cagctcgtgt cgtgagatgt tgggttaagt cccgcaacga gcgcaaccca cgtccttagt       1080
```

```
tgccatcatt cagttgggca ctctagggag actgccggtg ataagccgcg aggaaggtgt      1140
ggatgacgtc aagtcctcat ggcccttacg ggatgggcta cacacgtgct acaatggcgg      1200
tgacagtggg aggcgaagga gcgatctgga gcaaatcccc aaaagccgtc tcagttcgga      1260
ttgcactctg caactcgagt gcatgaaggc ggaatcgcta gtaatcgtgg atcagcatgc      1320
cacggtgaat acgttccgg gccttgtaca caccgcccgt cacaccatgg gagttggtct       1380
tacccgacgg cgctgcgcca accgcaagg                                        1409

<210> SEQ ID NO 14
<211> LENGTH: 1339
<212> TYPE: DNA
<213> ORGANISM: Methylobacterium L2-76
<220> FEATURE:
<221> NAME/KEY: misc_feature
<222> LOCATION: (56)..(56)
<223> OTHER INFORMATION: n is a, c, g, or t
<220> FEATURE:
<221> NAME/KEY: misc_feature
<222> LOCATION: (60)..(60)
<223> OTHER INFORMATION: n is a, c, g, or t

<400> SEQUENCE: 14
tgcagtcgaa cgggcttctt cggaagtcag tggcagacgg gtgagtaaca cgtggnaacn        60
tgcccttcgg ttcggaataa ctcagggaaa cttgagctaa taccggatac gcccttatgg       120
ggaaaggttt actgccgaag gatcggcccg cgtctgatta gcttgttggt ggggtaacgg       180
cctaccaagg cgacgatcag tagctggtct gagaggatga tcagccacac tgggactgag       240
acacggccca gactcctacg ggaggcagca gtggggaata ttggacaatg ggcgcaagcc       300
tgatccagcc atgccgcgtg agtgatgaag gccttagggt tgtaaagctc ttttgtccgg       360
gacgataatg acggtaccgg aagaataagc cccggctaac ttcgtgccag cagccgcggt       420
aatacgaagg gggctagcgt tgctcggaat cactgggcgt aaagggcgcg taggcggccg       480
attaagtcgg gggtgaaagc ctgtggctca accacagaat tgccttcgat actggttggc       540
ttgagaccgg aagaggacag cggaactgcg agtgtagagg tgaaattcgt agatattcgc       600
aagaacacca gtggcgaagg cggctgtctg gtccggttct gacgctgagg cgcgaaagcg       660
tggggagcaa acaggattag ataccctggt agtccacgcc gtaaacgatg aatgccagcc       720
gttggcctgc ttgcaggtca gtggcgccgc taacgcatta agcattccgc ctggggagta       780
cggtcgcaag attaaaactc aaaggaattg acggggcccc gcacaagcgg tggagcatgt       840
ggtttaattc gaagcaacgc gcagaacctt accatccctt gacatggcat gttacctcga       900
gagatcgggg atcctcttcg gaggcgtgca cacaggtgct gcatggctgt cgtcagctcg       960
tgtcgtgaga tgttgggtta agtcccgcaa cgagcgcaac ccacgtcctt agttgccatc      1020
attcagttgg gcactctagg gagactgccg gtgataagcc gcgaggaagg tgtggatgac      1080
gtcaagtcct catggccctt acgggatggg ctacacacgt gctacaatgg cggtgacagt      1140
gggacgcgaa accgcgaggt tgagcaaatc cccaaaagcc gtctcagttc ggattgcact      1200
ctgcaactcg gtgcatgaa ggcggaatcg ctagtaatcg tggatcagca cgccacggtg       1260
aatacgttcc cgggccttgt acaccgccgt cacaccatgg gagttggtct tacccga         1320 cggcgctgcg ccaaccgca                                                  1339

<210> SEQ ID NO 15
<211> LENGTH: 18
<212> TYPE: DNA
<213> ORGANISM: Artificial Sequence
```

```
<220> FEATURE:
<223> OTHER INFORMATION: primer for 16S rRNA genes

<400> SEQUENCE: 15
agagtttgat cmtggctc                                                  18

<210> SEQ ID NO 16
<211> LENGTH: 16
<212> TYPE: DNA
<213> ORGANISM: Artificial Sequence
<220> FEATURE:
<223> OTHER INFORMATION: primer for 16S rRNA genes

<400> SEQUENCE: 16
taccttgtta cgactt                                                    16

<210> SEQ ID NO 17
<211> LENGTH: 18
<212> TYPE: DNA
<213> ORGANISM: Artificial Sequence
<220> FEATURE:
<223> OTHER INFORMATION: primer for 16S rRNA genes

<400> SEQUENCE: 17
ggattagata ccctggta                                                  18

<210> SEQ ID NO 18
<211> LENGTH: 19
<212> TYPE: DNA
<213> ORGANISM: Artificial Sequence
<220> FEATURE:
<223> OTHER INFORMATION: primer for 16S rRNA genes

<400> SEQUENCE: 18
gtattaccgc ggctgctgg                                                 19

<210> SEQ ID NO 19
<211> LENGTH: 15
<212> TYPE: DNA
<213> ORGANISM: Artificial Sequence
<220> FEATURE:
<223> OTHER INFORMATION: primer for 16S rRNA genes

<400> SEQUENCE: 19
gggttgcgct cgttg                                                     15
```